United States Patent
Al-Qahtani

(10) Patent No.: US 12,116,326 B2
(45) Date of Patent: Oct. 15, 2024

(54) CONVERSION OF HYDROGEN SULFIDE AND CARBON DIOXIDE INTO HYDROCARBONS USING NON-THERMAL PLASMA AND A CATALYST

(71) Applicant: Saudi Arabian Oil Company, Dhahran (SA)

(72) Inventor: Mohammad S. Al-Qahtani, Hasa (SA)

(73) Assignee: Saudi Arabian Oil Company, Dhahran (SA)

( * ) Notice: Subject to any disclaimer, the term of this patent is extended or adjusted under 35 U.S.C. 154(b) by 401 days.

(21) Appl. No.: 17/456,065

(22) Filed: Nov. 22, 2021

(65) Prior Publication Data
US 2023/0159409 A1  May 25, 2023

(51) Int. Cl.
| | | |
|---|---|---|
| C07C 1/12 | (2006.01) | |
| B01J 8/00 | (2006.01) | |
| C01B 17/04 | (2006.01) | |

(52) U.S. Cl.
CPC .............. C07C 1/12 (2013.01); B01J 8/001 (2013.01); B01J 8/0015 (2013.01); C01B 17/0495 (2013.01); B01J 2219/0894 (2013.01)

(58) Field of Classification Search
CPC .. C07C 1/12; C07C 9/04; C07C 1/322; C07C 9/06; B01J 2219/0894; C01B 17/0495; C01B 17/0426; B01D 53/8618; B01D 53/869
See application file for complete search history.

(56) References Cited

U.S. PATENT DOCUMENTS

| | | |
|---|---|---|
| 880,404 A | 2/1908 | Sanford |
| 922,578 A | 5/1909 | Gries |
| 1,591,264 A | 7/1926 | Baash |
| 1,789,993 A | 1/1931 | Switzer |
| 1,896,482 A | 2/1933 | Crowell |

(Continued)

FOREIGN PATENT DOCUMENTS

| | | |
|---|---|---|
| AU | 636642 | 5/1993 |
| AU | 2004204512 | 7/2004 |

(Continued)

OTHER PUBLICATIONS

Liu et al., "Ni—Mo sulfide semiconductor catalyst with high catalytic activity for one step conversion of CO2 and H2s to Syngas in non-thermal plasma," Catalysts, Jun. 2019, 9(6):525, 13 pages.

(Continued)

*Primary Examiner* — Jafar F Parsa
(74) *Attorney, Agent, or Firm* — Fish & Richardson P.C.

(57) ABSTRACT

A feed stream is flowed to a catalytic reactor. The catalytic reactor includes a non-thermal plasma and a catalyst. The feed stream includes hydrogen sulfide and carbon dioxide. The feed stream is contacted with the catalyst in the presence of the non-thermal plasma at a reaction temperature, thereby converting the hydrogen sulfide and the carbon dioxide in the feed stream to produce a product. The product includes a hydrocarbon and sulfur. The product is separated into a product stream and a sulfur stream. The product stream includes the hydrocarbon from the product. The sulfur stream includes the sulfur from the product.

19 Claims, 5 Drawing Sheets

(56) References Cited

U.S. PATENT DOCUMENTS

| | | |
|---|---|---|
| 1,949,498 A | 3/1934 | Frederick et al. |
| 2,121,002 A | 6/1938 | Baker |
| 2,121,051 A | 6/1938 | Ragan et al. |
| 2,187,487 A | 1/1940 | Burt |
| 2,189,697 A | 2/1940 | Baker |
| 2,499,370 A | 3/1940 | De Groote et al. |
| 2,221,518 A | 11/1940 | Jennings |
| 2,222,233 A | 11/1940 | Mize |
| 2,286,075 A | 6/1942 | Evans |
| 2,304,793 A | 12/1942 | Bodine |
| 2,316,402 A | 4/1943 | Canon |
| 2,327,092 A | 8/1943 | Botkin |
| 2,383,674 A | 8/1945 | Osborne |
| 2,411,260 A | 11/1946 | Glover et al. |
| 2,546,978 A | 4/1951 | Collins et al. |
| 2,557,081 A | 6/1951 | De Groote et al. |
| 2,585,575 A | 2/1952 | Richard |
| 2,602,053 A | 7/1952 | De Groote et al. |
| 2,672,199 A | 3/1954 | McKenna |
| 2,707,998 A | 5/1955 | Baker et al. |
| 2,711,388 A | 6/1955 | Mottern et al. |
| 2,728,599 A | 12/1955 | Moore |
| 2,751,010 A | 6/1956 | Trahan |
| 2,758,477 A | 8/1956 | Albert |
| 2,825,026 A | 2/1958 | Holaday et al. |
| 2,881,838 A | 4/1959 | Morse et al. |
| 2,912,053 A | 11/1959 | Bruekelman |
| 2,912,273 A | 11/1959 | Chadderdon et al. |
| 2,915,127 A | 12/1959 | Abendroth |
| 2,965,175 A | 12/1960 | Ransom |
| 2,965,177 A | 12/1960 | Le Bus et al. |
| 3,075,242 A | 1/1963 | Emil |
| 3,116,799 A | 1/1964 | Lemons |
| 3,133,437 A | 5/1964 | Remke |
| 3,147,536 A | 9/1964 | Lamphere |
| 3,151,839 A | 10/1964 | Mott |
| 3,222,918 A | 12/1965 | Kuntz |
| 3,225,828 A | 12/1965 | Wisenbaker et al. |
| 3,340,186 A | 9/1967 | Weyl |
| 3,369,603 A | 2/1968 | Trantham |
| 3,381,748 A | 5/1968 | Peters et al. |
| 3,382,925 A | 5/1968 | Jennings |
| 3,415,744 A | 12/1968 | Buetow |
| 3,462,596 A | 8/1969 | Saunders |
| 3,482,603 A | 12/1969 | Outcalt |
| 3,528,775 A | 9/1970 | O'Hara et al. |
| 3,538,208 A | 11/1970 | Ohtsuka |
| 3,539,917 A | 11/1970 | Chleck |
| 3,546,926 A | 12/1970 | Dunavent et al. |
| 3,553,576 A | 1/1971 | Petitjean et al. |
| 3,752,877 A | 3/1971 | Beavon |
| 3,667,721 A | 6/1972 | Vujasinovic |
| 3,684,735 A | 8/1972 | De Groote et al. |
| 3,727,049 A | 4/1973 | Saunders |
| 3,763,840 A | 10/1973 | Schimmelpfenig |
| 3,778,706 A | 12/1973 | Thompson |
| 3,806,435 A | 4/1974 | Ohta |
| 3,817,278 A | 6/1974 | Elliott |
| 3,897,038 A | 7/1975 | Le Rouax |
| 3,915,426 A | 10/1975 | Le Rouax |
| 3,980,456 A | 9/1976 | Browall |
| 3,982,564 A | 9/1976 | Clabburn et al. |
| 4,001,386 A | 1/1977 | Klein et al. |
| 4,030,354 A | 6/1977 | Scott |
| 4,034,219 A | 7/1977 | Louden et al. |
| 4,042,019 A | 8/1977 | Henning |
| 4,059,155 A | 11/1977 | Greer |
| 4,084,306 A | 4/1978 | Barker |
| 4,099,699 A | 7/1978 | Allen |
| 4,157,247 A | 6/1979 | Collins, III et al. |
| 4,164,437 A | 8/1979 | Henne et al. |
| 4,178,358 A | 12/1979 | Smith et al. |
| 4,190,112 A | 2/1980 | Davis |
| 4,222,977 A | 9/1980 | Dobo |
| 4,229,154 A | 10/1980 | Chaban, Jr. et al. |
| 4,230,463 A | 10/1980 | Henis et al. |
| 4,253,928 A | 3/1981 | Blutas et al. |
| 4,254,983 A | 3/1981 | Harris |
| 4,276,931 A | 7/1981 | Murray |
| 4,296,822 A | 10/1981 | Ormsby |
| 4,301,400 A | 11/1981 | Paap |
| 4,317,729 A | 3/1982 | Yamashita et al. |
| 4,346,006 A | 8/1982 | Kopp |
| 4,349,071 A | 9/1982 | Fish |
| 4,362,677 A | 12/1982 | Yamashita et al. |
| 4,391,326 A | 7/1983 | Greenlee |
| 4,407,367 A | 10/1983 | Kydd |
| 4,412,130 A | 10/1983 | Winters |
| 4,413,642 A | 11/1983 | Smith et al. |
| 4,422,948 A | 12/1983 | Corley et al. |
| 4,430,219 A | 2/1984 | Kuzumoto et al. |
| 4,466,946 A | 8/1984 | Goddin, Jr. et al. |
| 4,467,996 A | 8/1984 | Baugh |
| 4,482,514 A | 11/1984 | Schindler |
| 4,526,662 A | 7/1985 | Bylery et al. |
| 4,537,701 A | 8/1985 | Oppenlaender et al. |
| 4,538,684 A | 9/1985 | Sheffield |
| 4,543,191 A | 9/1985 | Stewart et al. |
| 4,546,043 A | 10/1985 | Yoshimoto et al. |
| 4,562,888 A | 1/1986 | Collet |
| 4,581,134 A | 4/1986 | Richter, Jr. et al. |
| 4,589,896 A | 5/1986 | Chen et al. |
| 4,603,578 A | 8/1986 | Stoltz |
| 4,631,162 A | 12/1986 | Yoshimoto et al. |
| 4,664,808 A | 5/1987 | Kim |
| 4,696,502 A | 9/1987 | Desai |
| 4,701,187 A | 10/1987 | Choe |
| 4,717,407 A | 1/1988 | Choe et al. |
| 4,742,304 A | 5/1988 | Schnall et al. |
| 4,743,189 A | 5/1988 | Samuelson |
| 4,772,391 A | 9/1988 | Baker et al. |
| 4,797,550 A | 1/1989 | Nelson et al. |
| 4,820,460 A | 4/1989 | Repetti et al. |
| 4,830,640 A | 5/1989 | Nakamura et al. |
| 4,834,184 A | 5/1989 | Streich et al. |
| 4,850,847 A | 7/1989 | Samuelson |
| 4,861,661 A | 8/1989 | Samuelson |
| 4,869,321 A | 9/1989 | Hamilton |
| 4,898,245 A | 2/1990 | Braddick |
| 4,902,422 A | 2/1990 | Pinnau et al. |
| 4,915,886 A | 4/1990 | Repetti et al. |
| 4,938,902 A | 7/1990 | Nakamura et al. |
| 4,941,812 A | 7/1990 | Samelson |
| 4,950,391 A | 8/1990 | Weickhardt |
| 4,953,617 A | 9/1990 | Ross et al. |
| 4,959,160 A | 9/1990 | Lake |
| 4,980,061 A | 12/1990 | Tadros et al. |
| 4,990,165 A | 2/1991 | Bikson |
| 4,995,952 A | 2/1991 | Dandapani et al. |
| 5,012,863 A | 5/1991 | Springer |
| 5,023,069 A | 6/1991 | Serrand |
| 5,035,065 A | 7/1991 | Parkinson |
| 5,049,167 A | 9/1991 | Castro et al. |
| 5,067,345 A | 11/1991 | Mougne |
| 5,069,793 A | 12/1991 | Kaschemakat et al. |
| 5,084,349 A | 1/1992 | Sasaki |
| 5,085,676 A | 2/1992 | Ekiner et al. |
| 5,089,781 A | 2/1992 | Arichika et al. |
| 5,102,484 A | 4/1992 | Allen et al. |
| 5,117,909 A | 6/1992 | Wilton et al. |
| 5,129,956 A | 7/1992 | Christopher et al. |
| 5,151,227 A | 9/1992 | Nguyen |
| 5,159,981 A | 11/1992 | Le |
| 5,160,353 A | 11/1992 | Gochanour |
| 5,176,208 A | 1/1993 | Lalande et al. |
| 5,187,101 A | 2/1993 | Kato |
| 5,197,547 A | 3/1993 | Morgan |
| 5,242,636 A | 9/1993 | Sluma et al. |
| 5,246,597 A | 9/1993 | Jenson et al. |
| 5,259,239 A | 11/1993 | Gaisford |
| 5,294,553 A | 3/1994 | Kawahara |
| 5,295,541 A | 3/1994 | Ng et al. |
| 5,330,000 A | 7/1994 | Givens et al. |
| 5,330,348 A | 7/1994 | Aneja et al. |

(56) References Cited

U.S. PATENT DOCUMENTS

| | | |
|---|---|---|
| 5,356,461 A | 10/1994 | Sluma et al. |
| 5,358,048 A | 10/1994 | Brooks |
| 5,368,889 A | 11/1994 | Johnson et al. |
| 5,381,002 A | 1/1995 | Morrow et al. |
| 5,401,300 A | 3/1995 | Lokhandwala et al. |
| 5,407,466 A | 4/1995 | Lokhandwala et al. |
| 5,407,467 A | 4/1995 | Lokhandwala et al. |
| 5,431,877 A | 7/1995 | Brucken et al. |
| 5,439,626 A | 8/1995 | Bennett et al. |
| 5,454,258 A | 10/1995 | Capuano |
| 5,480,598 A | 1/1996 | Gentile et al. |
| 5,489,382 A | 2/1996 | Tatebe |
| 5,507,346 A | 4/1996 | Gano et al. |
| 5,531,865 A | 7/1996 | Cole |
| 5,556,589 A | 9/1996 | Sibal |
| 5,580,114 A | 12/1996 | Palmer |
| 5,598,874 A | 2/1997 | Alei et al. |
| 5,604,036 A | 2/1997 | Price et al. |
| 5,632,803 A | 5/1997 | Stoner |
| 5,643,660 A | 7/1997 | Price et al. |
| 5,678,635 A | 10/1997 | Dunlap et al. |
| 5,707,584 A | 1/1998 | Terpstra et al. |
| 5,779,897 A | 7/1998 | Kalthod et al. |
| 5,783,079 A | 7/1998 | Kumano et al. |
| 5,833,001 A | 11/1998 | Song et al. |
| 5,833,896 A | 11/1998 | Jacobs et al. |
| 5,837,032 A | 11/1998 | Moll et al. |
| 5,837,033 A | 11/1998 | Giglia et al. |
| 5,842,518 A | 12/1998 | Soybel et al. |
| 5,924,489 A | 7/1999 | Hatcher |
| 5,944,101 A | 8/1999 | Hearn |
| 6,019,115 A | 2/2000 | Sanders |
| 6,096,239 A | 8/2000 | Fung et al. |
| 6,138,764 A | 10/2000 | Scarsdale et al. |
| 6,179,900 B1 | 1/2001 | Behling et al. |
| 6,241,871 B1 | 6/2001 | Donini et al. |
| 6,247,542 B1 | 6/2001 | Kruspe et al. |
| 6,270,055 B1 | 8/2001 | Szeteli et al. |
| 6,276,452 B1 | 8/2001 | Davis et al. |
| 6,361,582 B1 | 3/2002 | Pinnau et al. |
| 6,364,940 B1 | 4/2002 | Prueter et al. |
| 6,371,204 B1 | 4/2002 | Singh et al. |
| 6,374,852 B1 | 4/2002 | Olivas |
| 6,402,813 B2 | 6/2002 | Monereau et al. |
| 6,443,180 B1 | 9/2002 | Samuelson et al. |
| 6,451,252 B1 | 9/2002 | Ruan et al. |
| 6,491,108 B1 | 12/2002 | Slup et al. |
| 6,521,025 B1 | 2/2003 | Shilton et al. |
| 6,551,088 B2 | 4/2003 | Nguyen et al. |
| 6,555,005 B1 | 4/2003 | Zha et al. |
| 6,595,289 B2 | 7/2003 | Tumlin et al. |
| 6,614,242 B2 | 9/2003 | Matter et al. |
| 6,623,637 B1 | 9/2003 | Monzen et al. |
| 6,630,069 B2 | 10/2003 | Sakashita et al. |
| 6,656,249 B1 | 12/2003 | Buisnnan |
| 6,660,377 B2 | 12/2003 | Bernaschek |
| 6,688,386 B2 | 2/2004 | Cornelssen |
| 6,768,106 B2 | 7/2004 | Gzara et al. |
| 6,797,209 B2 | 9/2004 | Travelute et al. |
| 6,805,730 B2 | 10/2004 | Herczeg |
| 6,808,023 B2 | 10/2004 | Smith et al. |
| 6,896,717 B2 | 5/2005 | Pinnau et al. |
| 6,899,178 B2 | 5/2005 | Tubel |
| 6,913,084 B2 | 7/2005 | Boyd |
| 7,001,664 B2 | 2/2006 | Travelute et al. |
| 7,036,531 B2 | 5/2006 | Manini et al. |
| 7,049,272 B2 | 5/2006 | Sinclair et al. |
| 7,096,950 B2 | 8/2006 | Howlett et al. |
| 7,117,956 B2 | 10/2006 | Grattan et al. |
| 7,172,075 B1 | 2/2007 | Ji |
| 7,188,674 B2 | 3/2007 | McGavern, III et al. |
| 7,188,675 B2 | 3/2007 | Reynolds |
| 7,231,975 B2 | 6/2007 | Lavaure et al. |
| 7,249,633 B2 | 7/2007 | Ravensbergen et al. |
| 7,284,611 B2 | 10/2007 | Reddy et al. |
| 7,306,735 B2 | 12/2007 | Baggott et al. |
| 7,393,195 B2 | 7/2008 | Keller et al. |
| 7,398,832 B2 | 7/2008 | Brisco |
| 7,405,182 B2 | 7/2008 | Verrett |
| 7,424,909 B2 | 9/2008 | Roberts et al. |
| 7,469,188 B2 | 12/2008 | Wee |
| 7,488,705 B2 | 2/2009 | Reddy et al. |
| 7,490,725 B2 | 2/2009 | Pinnau et al. |
| 7,497,260 B2 | 3/2009 | Telfer |
| 7,510,655 B2 | 3/2009 | Barnes |
| 7,591,305 B2 | 9/2009 | Brookey et al. |
| 7,600,572 B2 | 10/2009 | Slup et al. |
| 7,712,527 B2 | 5/2010 | Roddy |
| 7,762,323 B2 | 7/2010 | Frazier |
| 7,802,621 B2 | 9/2010 | Richards et al. |
| 7,901,646 B2 | 3/2011 | Ayala et al. |
| 7,934,552 B2 | 5/2011 | La Rovere |
| 7,965,175 B2 | 6/2011 | Yamano |
| 7,976,710 B2 | 7/2011 | Minhas et al. |
| 8,002,049 B2 | 8/2011 | Keese et al. |
| 8,043,418 B2 | 10/2011 | Ruud et al. |
| 8,069,916 B2 | 12/2011 | Giroux et al. |
| 8,075,951 B2 | 12/2011 | Cunningham et al. |
| 8,088,958 B2 | 1/2012 | Schucker |
| 8,101,086 B2 | 1/2012 | Varadaraj et al. |
| 8,104,624 B2 | 1/2012 | Chidambaran et al. |
| 8,115,481 B2 | 2/2012 | Chen |
| 8,119,007 B2 | 2/2012 | Bajpayee et al. |
| 8,197,673 B2 | 6/2012 | Khan |
| 8,318,017 B2 | 11/2012 | Fane et al. |
| 8,323,392 B2 | 12/2012 | Jones et al. |
| 8,361,200 B2 | 1/2013 | Sayari et al. |
| 8,376,051 B2 | 2/2013 | McGrath et al. |
| 8,397,765 B2 | 3/2013 | Jackson et al. |
| 8,424,688 B2 | 4/2013 | Chidambaran et al. |
| 8,453,724 B2 | 6/2013 | Zhou |
| 8,491,716 B2 | 7/2013 | Cho et al. |
| 8,491,792 B2 | 7/2013 | Kipp et al. |
| 8,496,055 B2 | 7/2013 | Mootoo et al. |
| 8,524,184 B2 | 9/2013 | Iyengar et al. |
| 8,551,199 B2 | 10/2013 | Thacker et al. |
| 8,579,024 B2 | 11/2013 | Mailand et al. |
| 8,685,236 B2 | 4/2014 | Miller |
| 8,716,689 B2 | 5/2014 | Chen et al. |
| 8,722,003 B1 | 5/2014 | Avagliano et al. |
| 8,726,983 B2 | 5/2014 | Khan |
| 8,770,276 B1 | 7/2014 | Nish et al. |
| 8,790,509 B2 | 7/2014 | Vu |
| 8,805,587 B1 | 8/2014 | Elshafei et al. |
| 8,828,121 B1 | 9/2014 | He et al. |
| 8,871,140 B2 | 10/2014 | Cho et al. |
| 8,899,338 B2 | 12/2014 | Elsayed et al. |
| 8,911,540 B2 | 12/2014 | Baer et al. |
| 9,092,124 B2 | 7/2015 | Amminudin et al. |
| 9,096,805 B2 | 8/2015 | Williams |
| 9,109,305 B2 | 8/2015 | Choi et al. |
| 9,109,433 B2 | 8/2015 | DiFoggio et al. |
| 9,133,671 B2 | 9/2015 | Kellner |
| 9,149,761 B2 | 10/2015 | Northrop et al. |
| 9,156,003 B2 | 10/2015 | Kelada |
| 9,157,035 B1 | 10/2015 | Ball, IV et al. |
| 9,181,499 B2 | 11/2015 | Mason et al. |
| 9,211,503 B2 | 12/2015 | Xiao et al. |
| 9,212,532 B2 | 12/2015 | Leuchtenberg et al. |
| 9,234,302 B2 | 1/2016 | Weber et al. |
| 9,234,394 B2 | 1/2016 | Wheater et al. |
| 9,244,017 B2 | 1/2016 | Cadieux et al. |
| 9,295,957 B2 | 5/2016 | Choi et al. |
| 9,353,220 B2 | 5/2016 | Savariar et al. |
| 9,359,861 B2 | 6/2016 | Burgos |
| 9,399,866 B2 | 7/2016 | Alawadhi |
| 9,410,066 B2 | 8/2016 | Ghassemzadeh |
| 9,416,617 B2 | 8/2016 | Wiese et al. |
| 9,427,699 B2 | 8/2016 | Mayer et al. |
| 9,428,404 B2 | 8/2016 | Bajpayee et al. |
| 9,435,571 B2 | 9/2016 | Ghoshal et al. |
| 9,448,221 B2 | 9/2016 | Duval et al. |
| 9,493,712 B2 | 11/2016 | Barroeta et al. |
| 9,551,200 B2 | 1/2017 | Read et al. |

(56) References Cited

U.S. PATENT DOCUMENTS

| | | |
|---|---|---|
| 9,555,345 B2 | 1/2017 | Al-shafei et al. |
| 9,574,417 B2 | 2/2017 | Laird et al. |
| 9,657,213 B2 | 5/2017 | Murphy et al. |
| 9,708,196 B2 | 7/2017 | Brenize et al. |
| 9,731,974 B2 | 8/2017 | Weiss et al. |
| 9,808,772 B2 | 11/2017 | Mochizuki |
| 9,861,910 B2 | 1/2018 | Hammad et al. |
| 9,863,571 B2 | 1/2018 | Critsinelis et al. |
| 10,087,752 B2 | 1/2018 | Bedouet |
| 9,927,169 B2 | 3/2018 | Baker et al. |
| 9,943,802 B1 | 4/2018 | Ballaguet et al. |
| 9,976,407 B2 | 5/2018 | Ash et al. |
| 10,022,677 B2 | 7/2018 | He et al. |
| 10,024,835 B2 | 7/2018 | Sreekumar |
| 10,106,410 B2 | 10/2018 | Ballaguet et al. |
| 10,106,411 B2 | 10/2018 | Ballaguet et al. |
| 10,188,988 B2 | 1/2019 | Debrock et al. |
| 10,197,545 B2 | 2/2019 | Sreekumar et al. |
| 10,240,431 B2 | 3/2019 | Caminari et al. |
| 10,260,010 B2 | 4/2019 | Soliman |
| 10,280,706 B1 | 5/2019 | Sharp, III |
| 10,301,898 B2 | 5/2019 | Orban |
| 10,365,049 B2 | 7/2019 | Tso et al. |
| 10,386,284 B2 | 8/2019 | Zhang |
| 10,472,576 B2 | 11/2019 | Salu et al. |
| 10,479,684 B2 | 11/2019 | Ballaguet et al. |
| 10,508,033 B2 | 12/2019 | Ballaguet et al. |
| 10,513,663 B2 | 12/2019 | Soliman et al. |
| 10,589,223 B1 | 3/2020 | Raynel et al. |
| 10,662,061 B1 | 5/2020 | Lithoxoos et al. |
| 10,682,606 B2 | 6/2020 | Choi |
| 10,765,995 B2 | 9/2020 | Hamad et al. |
| 10,889,766 B2 | 1/2021 | Barreau et al. |
| 10,889,915 B2 | 1/2021 | Choi et al. |
| 10,898,858 B2 | 1/2021 | Nagata et al. |
| 11,008,521 B2 | 5/2021 | Raynel et al. |
| 11,071,953 B2 | 7/2021 | Mochizuki et al. |
| 11,112,190 B2 | 9/2021 | Villette et al. |
| 11,131,660 B2 | 9/2021 | Ahmed et al. |
| 11,148,962 B2 | 10/2021 | Alghunaimi et al. |
| 2002/0053428 A1 | 5/2002 | Maples |
| 2002/0173209 A1 | 11/2002 | Travelute et al. |
| 2003/0047312 A1 | 3/2003 | Bell |
| 2003/0082096 A1 | 5/2003 | Lynn |
| 2003/0099594 A1 | 5/2003 | Lyon |
| 2003/0118763 A1 | 6/2003 | Travelute et al. |
| 2003/0132224 A1 | 7/2003 | Spencer |
| 2004/0010173 A1 | 1/2004 | Agarwal et al. |
| 2004/0050250 A1 | 3/2004 | Pinnau et al. |
| 2004/0086594 A1 | 5/2004 | Bernaschek |
| 2005/0037196 A1 | 2/2005 | Travelute et al. |
| 2005/0077243 A1 | 4/2005 | Pinnau et al. |
| 2005/0158235 A1 | 7/2005 | Ramani et al. |
| 2005/0167097 A1 | 8/2005 | Sommers et al. |
| 2005/0217479 A1 | 10/2005 | Hale et al. |
| 2006/0124531 A1 | 6/2006 | Behrendt et al. |
| 2006/0186340 A1 | 8/2006 | Lievois et al. |
| 2006/0286675 A1 | 12/2006 | Coleman et al. |
| 2007/0137528 A1 | 6/2007 | Le Roy-Ddelage et al. |
| 2007/0181304 A1 | 8/2007 | Rankin et al. |
| 2007/0183953 A1 | 8/2007 | Kerley et al. |
| 2008/0023863 A1 | 1/2008 | Lee et al. |
| 2008/0035215 A1 | 2/2008 | Loper |
| 2008/0236841 A1 | 10/2008 | Howlett et al. |
| 2008/0251253 A1 | 10/2008 | Lumbye |
| 2008/0268082 A1 | 10/2008 | Keller et al. |
| 2008/0295691 A1 | 12/2008 | Liu et al. |
| 2009/0115078 A1 | 5/2009 | Leister |
| 2009/0179636 A1 | 7/2009 | Chen |
| 2009/0194290 A1 | 8/2009 | Parks et al. |
| 2009/0250220 A1 | 10/2009 | Stamoulis |
| 2009/0277837 A1 | 11/2009 | Liu et al. |
| 2010/0221522 A1 | 9/2010 | Mrozinski |
| 2010/0260551 A1 | 10/2010 | Jespersen et al. |
| 2010/0264014 A1 | 10/2010 | Mignon et al. |
| 2010/0270018 A1 | 10/2010 | Howlett |
| 2011/0036570 A1 | 2/2011 | La Rovere et al. |
| 2011/0056681 A1 | 3/2011 | Khan |
| 2011/0067869 A1 | 3/2011 | Bour et al. |
| 2011/0073206 A1 | 3/2011 | Na |
| 2011/0138854 A1 | 6/2011 | Huang et al. |
| 2011/0168411 A1 | 7/2011 | Braddick |
| 2011/0185896 A1 | 8/2011 | Sethna et al. |
| 2011/0194105 A1 | 8/2011 | LaFrancois et al. |
| 2011/0198287 A1 | 8/2011 | Dukes et al. |
| 2011/0259609 A1 | 10/2011 | Hessels et al. |
| 2011/0278021 A1 | 11/2011 | Travis et al. |
| 2011/0290709 A1 | 12/2011 | Ohno |
| 2011/0308707 A1 | 12/2011 | Montoya |
| 2011/0309463 A1 | 12/2011 | Kruglick |
| 2012/0012335 A1 | 1/2012 | White et al. |
| 2012/0012804 A1 | 1/2012 | Chen |
| 2012/0111051 A1 | 5/2012 | Kulkarni et al. |
| 2012/0118571 A1 | 5/2012 | Zhou |
| 2012/0125850 A1 | 5/2012 | Fujimura et al. |
| 2012/0151890 A1 | 6/2012 | Pearson |
| 2012/0168154 A1 | 7/2012 | Chinn et al. |
| 2012/0170406 A1 | 7/2012 | DiFoggio et al. |
| 2012/0273367 A1 | 11/2012 | Themy et al. |
| 2012/0297665 A1 | 11/2012 | Goerz, Jr. et al. |
| 2012/0304862 A1 | 12/2012 | Taylor |
| 2012/0323059 A1 | 12/2012 | Liu et al. |
| 2013/0104772 A1 | 5/2013 | Schabron et al. |
| 2013/0105391 A1 | 5/2013 | Friese |
| 2013/0110411 A1 | 5/2013 | Black et al. |
| 2013/0213892 A1 | 8/2013 | Henthorne et al. |
| 2013/0240207 A1 | 9/2013 | Frazier |
| 2013/0277551 A1 | 10/2013 | Bourrel et al. |
| 2013/0296199 A1 | 11/2013 | Ghassemzadeh |
| 2014/0076793 A1 | 3/2014 | Ryu |
| 2014/0246382 A1 | 9/2014 | Matza et al. |
| 2014/0262953 A1 | 9/2014 | Ng et al. |
| 2014/0291887 A1 | 10/2014 | Coan |
| 2014/0338395 A1 | 11/2014 | Oelfke et al. |
| 2015/0042004 A1 | 2/2015 | Sumi |
| 2015/0044105 A1* | 2/2015 | Novoselov ............. B01J 19/088 |
| | | 422/186.04 |
| 2015/0060364 A1 | 3/2015 | McCutcheon et al. |
| 2015/0106027 A1 | 4/2015 | Koseoglu et al. |
| 2015/0136234 A1 | 5/2015 | Zulfiquar |
| 2015/0152340 A1 | 6/2015 | Cherney et al. |
| 2015/0175904 A1 | 6/2015 | Yeganeh et al. |
| 2015/0225261 A1 | 8/2015 | McGinnis |
| 2015/0225655 A1 | 8/2015 | Adams et al. |
| 2015/0231555 A1 | 8/2015 | He et al. |
| 2015/0240717 A1 | 8/2015 | Starcher et al. |
| 2015/0241139 A1 | 8/2015 | McGinnis |
| 2015/0265972 A1 | 9/2015 | Roesink |
| 2015/0265974 A1 | 9/2015 | Kurashina |
| 2015/0267127 A1 | 9/2015 | Yeganeh et al. |
| 2015/0290575 A1 | 10/2015 | Rothermel et al. |
| 2015/0298436 A1 | 10/2015 | Baer et al. |
| 2015/0298972 A1 | 10/2015 | Ballaguet et al. |
| 2016/0018049 A1 | 1/2016 | Yodogawa et al. |
| 2016/0121258 A1 | 5/2016 | First |
| 2016/0185596 A1 | 6/2016 | Manenti |
| 2016/0195344 A1 | 7/2016 | Tomita et al. |
| 2016/0228813 A1 | 8/2016 | Schwartz |
| 2016/0237810 A1 | 8/2016 | Beaman et al. |
| 2016/0281458 A1 | 9/2016 | Greenlee |
| 2016/0288058 A1 | 10/2016 | Tai et al. |
| 2016/0303521 A1 | 10/2016 | Chakraborty et al. |
| 2016/0305215 A1 | 10/2016 | Harris et al. |
| 2016/0346739 A1 | 12/2016 | Panglisch et al. |
| 2016/0370250 A1 | 12/2016 | Hiraoka |
| 2017/0036171 A1 | 2/2017 | Liehard |
| 2017/0044864 A1 | 2/2017 | Sabins et al. |
| 2017/0045290 A1 | 2/2017 | Ploeger et al. |
| 2017/0058628 A1 | 3/2017 | Van Wijk et al. |
| 2017/0067313 A1 | 3/2017 | Connell et al. |
| 2017/0190574 A1 | 7/2017 | Ercan et al. |
| 2017/0254793 A1 | 9/2017 | Al-Amri |
| 2017/0312682 A1 | 11/2017 | Keller |
| 2017/0319984 A1 | 11/2017 | Oshinowo |

(56) References Cited

U.S. PATENT DOCUMENTS

| | | |
|---|---|---|
| 2017/0320736 A1 | 11/2017 | Voss et al. |
| 2017/0333835 A1 | 11/2017 | Sano |
| 2017/0341017 A1 | 11/2017 | Dutta |
| 2017/0369791 A1 | 12/2017 | Khan et al. |
| 2018/0031524 A1 | 2/2018 | Hassell et al. |
| 2018/0057974 A1 | 3/2018 | Iwai |
| 2018/0066194 A1 | 3/2018 | Soliman et al. |
| 2018/0171249 A1 | 6/2018 | Fridman et al. |
| 2018/0179097 A1 | 6/2018 | Navarro et al. |
| 2018/0187095 A1 | 7/2018 | Soliman et al. |
| 2018/0187498 A1 | 7/2018 | Soto et al. |
| 2018/0195010 A1 | 7/2018 | Salu et al. |
| 2018/0202726 A1 | 7/2018 | Tso et al. |
| 2018/0216016 A1 | 8/2018 | Bakas et al. |
| 2018/0243699 A1 | 8/2018 | Sengupta |
| 2018/0243783 A1 | 8/2018 | Marschke et al. |
| 2018/0245427 A1 | 8/2018 | Jimenez et al. |
| 2018/0291282 A1 | 10/2018 | Soliman |
| 2018/0365555 A1 | 12/2018 | Aslam |
| 2018/0371876 A1 | 12/2018 | Lopez et al. |
| 2019/0009207 A1 | 1/2019 | Choi et al. |
| 2019/0010052 A1 | 1/2019 | Ballaguet et al. |
| 2019/0016598 A1 | 1/2019 | Ballaguet et al. |
| 2019/0022592 A1 | 1/2019 | Choi |
| 2019/0024473 A1 | 1/2019 | Arefi |
| 2019/0027615 A1 | 1/2019 | Zheng et al. |
| 2019/0049017 A1 | 2/2019 | Mcadam |
| 2019/0062645 A1 | 2/2019 | Al Seraihi et al. |
| 2019/0136113 A1 | 5/2019 | Holtsclaw et al. |
| 2019/0187015 A1 | 6/2019 | Sugita |
| 2019/0194526 A1 | 6/2019 | Holtsclaw et al. |
| 2019/0211274 A1 | 7/2019 | Soliman et al. |
| 2019/0227020 A1 | 7/2019 | Tamida et al. |
| 2019/0233972 A1 | 8/2019 | Choi et al. |
| 2019/0240613 A1 | 8/2019 | Raynel et al. |
| 2019/0247770 A1 | 8/2019 | Oshinowo |
| 2019/0316424 A1 | 10/2019 | Robinchaux et al. |
| 2019/0353356 A1 | 11/2019 | Fischer |
| 2020/0023310 A1 | 1/2020 | Luo et al. |
| 2020/0028053 A1 | 1/2020 | Strano |
| 2020/0040263 A1 | 2/2020 | Khuzzan et al. |
| 2020/0368678 A1 | 11/2020 | Choi |
| 2021/0354091 A1 | 1/2021 | Choi |
| 2021/0031139 A1 | 2/2021 | Hamad et al. |
| 2021/0047754 A1 | 2/2021 | Choi et al. |
| 2021/0080446 A1 | 3/2021 | Ahmed |
| 2021/0172689 A1 | 6/2021 | Villette |
| 2021/0189260 A1 | 6/2021 | Robert |
| 2021/0252459 A1 | 8/2021 | Choi et al. |
| 2021/0252460 A1 | 8/2021 | Choi et al. |
| 2021/0252461 A1 | 8/2021 | Choi et al. |
| 2021/0363032 A1 | 11/2021 | Robert et al. |
| 2021/0395619 A1 | 12/2021 | Raynel et al. |
| 2021/0396731 A1 | 12/2021 | Ahmed et al. |
| 2023/0183588 A1 | 6/2023 | Al-Qahtani |

FOREIGN PATENT DOCUMENTS

| | | |
|---|---|---|
| AU | 2007249417 | 11/2007 |
| AU | 2016214075 | 2/2020 |
| CA | 2734032 | 6/2016 |
| CA | 2968601 | 6/2016 |
| CN | 87106272 | 3/1988 |
| CN | 1049108 | 2/1991 |
| CN | 1189392 | 8/1998 |
| CN | 1386563 | 12/2002 |
| CN | 1751767 | 3/2006 |
| CN | 1844066 | 10/2006 |
| CN | 100411721 | 8/2008 |
| CN | 101522595 | 9/2009 |
| CN | 102068915 | 5/2011 |
| CN | 102085454 | 6/2011 |
| CN | 101658763 | 8/2011 |
| CN | 202595365 | 12/2012 |
| CN | 103980950 | 8/2014 |
| CN | 104001408 | 8/2014 |
| CN | 104520411 | 4/2015 |
| CN | 205534838 | 8/2016 |
| CN | 105974098 | 9/2016 |
| CN | 106731873 | 5/2017 |
| CN | 108640389 | 10/2018 |
| CN | 109696372 | 4/2019 |
| CN | 109882683 | 6/2019 |
| CN | 110127623 | 8/2019 |
| CN | 110237719 | 9/2019 |
| CN | 110237720 | 9/2019 |
| CN | 110280941 | 9/2019 |
| CN | 110711995 | 1/2020 |
| CN | 111167317 | 5/2020 |
| CN | 111365568 | 7/2020 |
| CN | 111412391 | 7/2020 |
| DE | 756808 | 6/1953 |
| DE | 102004010650 | 9/2005 |
| DK | 2236742 | 8/2017 |
| EP | 0181850 | 5/1986 |
| EP | 0230683 | 8/1987 |
| EP | 033076 | 8/1989 |
| EP | 0195447 | 10/1989 |
| EP | 586559 | 3/1994 |
| EP | 0684066 | 11/1995 |
| EP | 767259 | 4/1997 |
| EP | 2591847 | 5/2013 |
| EP | 2674210 | 12/2013 |
| EP | 2735856 | 5/2014 |
| EP | 2826545 | 1/2015 |
| EP | 2932239 | 10/2015 |
| EP | 3254010 | 12/2017 |
| EP | 3595801 | 1/2020 |
| EP | 2932248 | 2/2020 |
| FR | 2675709 | 10/1992 |
| FR | 2676006 | 11/1992 |
| GB | 908527 | 10/1962 |
| GB | 1374010 | 11/1974 |
| GB | 2336668 | 10/1999 |
| GB | 2392183 | 2/2004 |
| GB | 2453279 | 1/2009 |
| GB | 2492663 | 1/2014 |
| IN | 215089 | 2/2008 |
| JP | S56162001 | 12/1981 |
| JP | S 6140555 | 2/1986 |
| JP | S6418407 | 1/1989 |
| JP | S6422308 | 1/1989 |
| JP | H04227030 | 8/1992 |
| JP | H08281085 | 10/1996 |
| JP | H0938474 | 2/1997 |
| JP | 2001133450 | 5/2001 |
| JP | 2001190936 | 7/2001 |
| JP | 3250644 | 1/2002 |
| JP | 3764701 | 4/2006 |
| JP | 2008161755 | 7/2008 |
| JP | 2001040566 | 2/2011 |
| JP | 2015140498 | 8/2015 |
| KR | 20020003424 | 1/2002 |
| KR | 20110134562 | 12/2011 |
| KR | 20140059560 | 5/2014 |
| KR | 20160001142 | 1/2016 |
| KR | 101648843 | 8/2016 |
| KR | 101947311 | 5/2019 |
| KR | 102128754 | 7/2020 |
| SU | 1183890 | 10/1985 |
| TW | I579034 | 4/2017 |
| WO | WO 1989012728 | 12/1989 |
| WO | WO 93025636 | 12/1993 |
| WO | WO 9706880 | 2/1997 |
| WO | WO 2002090711 | 11/2002 |
| WO | WO 2004022796 | 3/2004 |
| WO | WO 2005028080 | 3/2005 |
| WO | WO 2005037883 | 4/2005 |
| WO | WO 2009111008 | 9/2009 |
| WO | WO 2010132807 | 11/2010 |
| WO | WO 2010133315 | 11/2010 |
| WO | WO 2011069192 | 6/2011 |
| WO | WO 2012004865 | 1/2012 |
| WO | WO 2012164023 | 12/2012 |

(56) References Cited

FOREIGN PATENT DOCUMENTS

| | | |
|---|---|---|
| WO | WO 2013068320 | 5/2013 |
| WO | WO 2013108885 | 7/2013 |
| WO | WO 2013146796 | 10/2013 |
| WO | WO 2014104124 | 7/2014 |
| WO | WO 2014177697 | 11/2014 |
| WO | WO 2015002523 | 1/2015 |
| WO | WO 2015074739 | 5/2015 |
| WO | WO 2016069722 | 5/2016 |
| WO | WO 2016086102 | 6/2016 |
| WO | WO 2016102568 | 6/2016 |
| WO | WO 2017001260 | 1/2017 |
| WO | WO 2017008748 | 1/2017 |
| WO | WO 2017020919 | 2/2017 |
| WO | WO 2017099671 | 6/2017 |
| WO | WO 2017220655 | 12/2017 |
| WO | WO 2018022756 | 2/2018 |
| WO | WO 2018097718 | 5/2018 |
| WO | WO 2018129228 | 7/2018 |
| WO | WO 2018165512 | 9/2018 |
| WO | WO 2018167221 | 9/2018 |
| WO | WO 2018169903 | 9/2018 |
| WO | WO 2018236644 | 12/2018 |
| WO | WO 2019001069 | 1/2019 |
| WO | WO 2019132877 | 7/2019 |
| WO | WO 2019171409 | 9/2019 |
| WO | WO 2020187888 | 9/2020 |
| WO | WO 2020225060 | 11/2020 |
| WO | WO 2020225061 | 11/2020 |
| WO | WO 2020225062 | 11/2020 |
| WO | WO 2020225063 | 11/2020 |
| WO | WO 2021113572 | 6/2021 |
| WO | WO 2021130530 | 7/2021 |

OTHER PUBLICATIONS

Tripodi et al., "Carbon dioxide methanation: design of a fully integrated plant," Energy & Fuels, 2020, 34:7242-7256, 15 pages.
Zhao et al., "Highly selective conversion of H2S—CO2 to syngas by combination of non-thermal plasma and MoS2/Al2O3," Journal of CO2 Utilization, 2020, 37:45-54, 10 pages.
Zhao et al., "Production of hyrdrogen and sulfur from hydrogen sulfide in a nonthermal-plasma pulsed corona discharge reactor," Chemical Engineering Science, 2007, 62:2216-2227, 12 pages.
PCT International Search Report and Written Opinion in International Appln. No. PCT/US2022/050089, dated Mar. 23, 2023, 14 pages.
U.S. Appl. No. 16/704,973, Villete et al., filed Dec. 15, 2019.
U.S. Appl. No. 16/741,853, Raynel et al., filed Jan. 24, 2020.
U.S. Appl. No. 17/009,573, Villete et al., filed Sep. 1, 2020.
U.S. Appl. No. 17/009,579, Villete et al., filed Sep. 1, 2020.
U.S. Appl. No. 17/103,685, Villete et al., filed Nov. 24, 2020.
U.S. Appl. No. 17/166,821, Lithoxoos et al., filed Feb. 3, 2021.
Abiev et al., "Non-thermal plasma for process and energy intensification in dry reforming of methane," Catalysts, Nov. 2020, 10:1358, 39 pages.
Abrams et al., "Use of seawater in flue gas desulfurization," JAPCA, 1988, 38(7):969-974, 7 pages.
Adamczak et al, "Preparation of polymeric membranes by in situ interfacial polymerization," International Journal of Polymer Science, 2019, 14 pages.
Ahmed et al., "Use of Transverse Flow Hollow Fibers for Bubble-less Membrane Aeration," Elsevier Science Ltd, 1996, 30(2):440-446, 7 pages.
Akhondi et al., "The Performance and Fouling Control of Submerged Hollow Fiber (HF) Systems: A Review," Applied Sciences, 2017, 7, 765, 39 pages.
Albo et al., "Absorption of coal combustion flue gases in ionic liquids using different membrane contactors," Desalination and Water Treatment, 2011, 27:54-59, 6 pages.
AlQahtani et al., "One-Step Low-Temperature Reduction of Sulfur Dioxide to Elemental Sulfur by Plasma-Enhanced Catalysis," ACS Catal., 2020, 10:5272-5277, 6 pages.

AlQahtani et al., "Plasma-assisted catalytic reduction of SO2 to elemental sulfur: Influence of nonthermal plasma and temperature on iron sulfide catalyst," Journal of Catalysis, Nov. 2020, 391:260-272, 13 pages.
Amo et al., "Low-Quality Natural Gas Sulfur Removal/Recovery," Membrane Technology and Research, DOE Report DE-AC21-92MC28133-01, Jan. 29, 1998, 107 pages.
An et al., "Synthesis and SO2 Absorption/Desorption Properties of Poly(1,1,3,3-tetramethylguanidine acrylate)," Macromolecules, Apr. 2007, 40(9):3388-3393.
Andreasen et al., "Use of Seawater Scrubbing for SO2 Removal from Marine Engine Exhaust Gas", Energy & Fuels, 2007, 21:3274-3279, 6 pages.
Aschoundong et al., "Silane Modification of Cellulose Acetate Dense Films as Materials for Acid Gas Removal Macromolecules," Macromolecules, 2013, 46(14):5584-5594, 11 pages.
ASTM, "D 3921-85: Standard test method for oil and grease and petroleum hydrocarbons in water," ASTM International, 1985 (reapproved 1990), 5 pages.
ASTM, "D 4281-95: Standard test method for oil and grease (fluorocarbon extractable substances) by gravimetric determination," ASTM International, 1995 (reapproved 2005), 6 pages.
ASTM, "D 7066-04, Standard test method for dimer/trimer of chlorotrifluoroethylene (S-316) recoverable oil and grease and nonpolar by Infrared determination," ASTM International, 2007, 9 pages.
Bajpayee et al., "Very low temperature membrane-free desalination by directional solvent extraction," Energy & Environmental Science, 4: 2011, 1672-1675, 4 pages.
Ballaguet et al., "Sulphur Cycle," Encyclopedia of Hydrocarbons, Istituto Della Enciclopedia Italiana Fondata Da Giovanni Treccani Spa, vol. II Refining and Petrochemicals, Chapter 3.2, 2006, 43 pages.
Belfort et al., "The behavior of suspensions and macromolecular solutions in crossflow microfiltration," J. Membr. Sci., 1994, 96, 58 pages.
Belov et al., "Gas transport and free volume in hexafluoropropylene polymers," Journal of Membrane Science, Nov. 2011, 383:70-77, 8 pages.
Ben-Shebil, "Effect of heat of adsorption on the adsorptive drying of solvents at equilibrium in a packed bed of zeolite," Chemical Engineering Journal, Jul. 1999, 74(3):197-204, 8 pages.
Bernardo et al., "Gas transport properties of Pebax/room temperature ionic liquid gel membranes" Separation and Purification Technology, Sep. 2012, 97:73-82, 10 pages.
Bhide et al., "Hybrid processes for the removal of acid gases from natural gas," Journal of Membrane Science, 1998, 140(1):27-49, 23 pages.
Bogaerts et al., "CO2 conversion by plasma technology: Insights from modeling the plasma chemistry and plasma reactor design," Plasma Sources Science and Technology, May 2017, 26(6):063001, 35 pages.
Bogaerts et al., "Plasma-based conversion of CO2: Current status and future challenges," Faraday Discussions, 2015, 183:217-232, 16 pages.
Bonyadi et al., "Flux enhancement in membrane distillation by fabrication of dual layer hydrophilic-hydrophobic hollow fiber membranes," Journal of membrane science, 2007, 306(1-2):134-146, 13 pages.
Boo et al., "Membrane-less and Non-Evaporative Desalination of Hypersaline Brines by Temperature Swing Solvent Extraction," Environmental Science & Technology Letters, 6: 2019, 359-364, 6 pages.
Bothamley, "Quantifying Oil/water Separation Performance in Three-Phase Separators—Part 1," Mar. 22, 2017, Mark Bothamley Consulting LLC., 14 pages.
Boyle et al., "Applicability Statement for Traffic Engineering with MPLS" RFC 3346, Nework Working Group, Aug. 2002, 14 pages.
Bruton et al., "Whipstock Options for Sidetracking," Oilfield Review, 2014, 26(1), 10 pages.
Cerneaux et al., "Comparison of various membrane distillation methods for desalination using hydrophobic ceramic membranes," Journal of membrane science, 2009, 337(1-2):55-60.

(56) References Cited

OTHER PUBLICATIONS

Chatterjee et al., "Poly(ether urethane) and poly(ether urethane urea) membranes with high H2S/CH4 selectivity," Journal of Membrane Science, Nov. 1997, 135:99-106, 8 pages.

Chen et al., "High CO2 permeability of ceramic-carbonate dual-phase hollow fiber membrane at medium-high temperature", Journal of Membrane Science, Mar. 2020, 597:117770.

Chen et al., "Tubular hydrophobic ceramic membrane with asymmetric structure for water desalination via vacuum membrane distillation process," Desalination, 2018, 443:212-220, 9 pages.

Cheng et al., "Modeling and optimization of hollow fiber DCMD module for desalination," Journal of Membrane Science, 2008, 318(1-2):154-166, 13 pages.

Cheng et al., "Response surface modeling and optimization of direct contact membrane distillation for water desalination," Desalination, 2016, 394:108-122, 15 pages.

Cho et al., "Comparison of hollow fiber membranes in direct contact and air gap membrane distillation," Desalination and Water Treatment, 2015, 9 pages.

Choi et al., "Effect of aeration on CaSO4 scaling in membrane distillation process," Desalination and Water Treatment, 2017, 90:7-15, 10 pages.

Chou et al., "Characteristics and potential applications of a novel forward osmosis hollow fiber membrane," Desalination, 2010, 261, 8 pages.

Christopoulos, "Reliable computations of knee point for a curve and introduction of a unit invariant estimation," National and Kapodistrian University of Athens, Dec. 2014, 9 pages.

Cirne et al., "Methods for Determination of Oil and Grease Contents in Wastewater from the Petroleum Industry," Chemistry and Chemical Technology, 2016, 10(4):437-444, 8 pages.

Collins English Dictionary, Complete and Unabridged, "Spacer," Harper Collins Publishers 12th Edition, 2014, 1 page.

Cui et al., "Removal of organic micro-pollutants (phenol, aniline and nitrobenzene) via forward osmosis (FO) process: Evaluation of FO as an alternative method to reverse osmosis (RO)," Water Research, Mar. 2016, 91:104-114, 48 pages.

Cui et al., "Ultrahigh and Selective SO2 Uptake in Inorganic Anion-Pillared Hybrid Porous Materials," Advanced Materials, May 2017, 29(28):1606929, 9 pages.

Culfaz et al., "Microstructured hollow fibers for ultrafiltration," Journal of Membrane Science, Feb. 2010, 347(1-2):32-41, 10 pages.

Curcio et al. "Hybrid nanofiltration—membrane crystallization system for the treatment of sulfate wastes," Journal of Membrane Science, 2010, 360(1-2):493-498, 6 pages.

Dang et al., "Research on decomposition of hydrogen sulfide using non-thermal plasma with metal oxide catalysis," Energy Procedia, 2012, 16:856-862, 7 pages.

Davison et al., "Structure and Amine-Water Solubility in Desalination by Solvent Extraction," Journal of Chemical & Engineering Data, 5: 1960, 420-423, 4 pages.

Dayarathne et al., "Enhancement of cleaning-in-place (CIP) of a reverse osmosis desalination process with air micro-nano bubbles," Desalination, 2017, 422, 1-4, 4 pages.

De Bie et al., "Fluid modeling of the conversion of methane into higher hydrocarbons in an atmospheric pressure dielectric barrier discharge," Plasma Processes and Polymers, 2011, 8(11):1033-1058, 26 pages.

Decher et al., "Layer-by-layer assembled multicomposite films," Current Opinion in Colloid & Interface Science, 1998, 3:32-39, 8 pages.

Delfino et al., "A simple and fast method to determine water content in biodiesel by electrochemical impedance spectroscopty," Talanta, 2018, 179:753-759, 26 pages.

DeMontigny et al., "Comparing the Absorption Performance of Packed cols. and Membrane Contactors," Industrial & Engineering Chemistry Research, 44: 2005, 5726-5732, 7 pages.

Dindore et al., "Hollow fiber membrane contactor as a gas-liquid model contactor," Chemical Engineering Science, 60: 2005, 467-479, 14 pages.

Ding et al., "Fabrication of high performance Matrimid/polysulfone dual-layer hollow fiber membranes for O2/N2 separation," Journal of Membrane Science, 2008, 323:352-361, 10 pages.

Diomede et al., "Insight into CO dissociation in plasmas from numerical solution of a vibrational diffusion equation," J. Phys. Chem. C, Aug. 2017, 121(36):19568-19576, 46 pages.

Ekiner et al., "Polyamide hollow fibers for hydrogen/methane separation—spinning and properties," Journal of Membrane Science, 1990, 53, 15 pages.

Elinoff et al, "Thermal diode can control direction of heat flow," Electronic Products Magazine, Apr. 2017, 2 pages.

EPA Method 1664, revision A, "N-Hexane extractable material (HEM; Oil and Grease) and silica gel treated n-hexane extractable material (SGT-HEM; Non-polar material) by extraction and gravimetry," United States Environmental Protection Agency, Office of Water, Washington D.C., EPA-821-R-98- 002, PB99-121949, Feb. 1999, 28 pages.

EPA Method 413.1, "Oil and Grease (Gravimetric, Separatory Funnel Extraction)," Issued in 1974, Editorial revision 1978, Standard test method for oil and grease using gravimetric determination, 3 pages.

EPA Method 413.2, "Oil and Grease (Spectrophotometric, Infrared)," Issued in 1974, Editorial revision 1978, Standard test method for Oil and grease analysis using Freon extraction and IR absorbance without the Freon extract being treated by silica gel, 3 pages.

EPA Method 418.1, "Petroleum Hydrocarbons (Spectrophotometric, Infrared)," Issued in 1978, 3 pages.

Fane et al., "A review of fouling and fouling control in ultrafiltration," Desalination, 1987, 62:117-136, 20 pages.

Fang et al., "Interfacially polymerized composite nanofiltration hollow fiber membranes for low-pressure water softening," Journal of Membrane Science, 2013, 430:129-139, 11 pages.

Findley, "Vaporization through porous membranes," Industrial & Engineering Chemistry Process Design and Development, 1967, 6(2):226-230, 5 pages.

Fortuny et al., "Measuring Salinity in crude oils: Evaluation of methods and an improved performance," Fuel, 2008, 87:1241-1248, 9 pages.

Francis et al., "Performance of different hollow fiber membranes for seawater desalination using membrane distillation," Desalination and Water Treatment, 2015, 55(10):2786-2791, 10 pages.

Froschauer et al., "No Matter of Course: Ionic Liquids as SO2-Selective Gas Absorbers," Lenzinger Berichte, Jan. 2013, 91:30-43, 15 pages.

Gabrus et al., "Experimental studies on 3A and 4A zeolite molecular sieves regeneration in TSA process: Aliphatic alcohols dewatering-water desorption," Chemical Engineering Journal, Jan. 2015, 259:232-242, 11 pages.

Garcia-Fernandez et al., "Mechanism of formation of hollow fiber membranes for membrane distillation: 1. Inner coagulation power effect on morphological characteristics," Journal of Membrane Science, 542: 2017, 456-468, 13 pages.

Glasoe et al., "Solubility of water and deuterium oxide in carbon tetrachloride, toluene, and cyclohexane at various temperatures," Journal of Chemical & Engineering Data, 17(1), pp. 66-68, 1972, 3 pages.

Gryta et al., "Concentration of saline wastewater from the production of heparin," Desalination, 2000, 129(1):35-44, 10 pages.

Hanbury et al., "Membrane distillation—an assessment," Desalination, 1985, 56:287-297, 11 pages.

Hasenberg, "Sulfur Dioxide," in G. Kreysa and M. Schutze, Corrosion Handbook, vol. 10: Sulfur Dioxide, sodium sulfate, p. 5-37. Weinheim: Wiley, May 2008.

Hatcher et al., "Sour water stripping Part 2: phenolic water—Digital Refining," Digitalrefining.com, Aug. 2014, 5 pages.

He et al., "An improved resistance model for gas permeation in composite membranes," Journal of Membrane Science, 1996, 118:1-7, 7 pages.

Heijkers et al., "Plasma-based CH4 conversion into higher hydrocarbons and H2: Modeling to reveal the reaction mechanisms of different plasma sources," Journal of Physical Chemistry, May 2020, 124:7016-7030, 15 pages.

(56) References Cited

OTHER PUBLICATIONS

Henis et al., "Composite hollow fiber membranes for gas separation: the resistance model approach," Journal of Membrane Science, 1981, 8:233-246, 14 pages.
Hibbard et al., "NACA Research Memorandum: Solubility of Water in Hydrocarbons," National Advisory Committee for Aeronautics, Washington, Jul. 10, 1952, 27 pages.
Hoff et al., "CO2 absorption with membrane contactors vs. packed absorbers—Challenges and opportunities in post combustion capture and natural gas sweetening," Energy Procedia, 2013, 37:952-960, 9 pages.
Hsu et al., "Seawater desalination by direct contact membrane distillation," Desalination, 2002, 143(3):279-287, 9 pages.
Huang et al., "Facilitated separation of CO2 and SO2 through supported liquid membranes using carboxylate-based ionic liquids," Journal of Membrane Science, Dec. 2014, 471:227-236, 10 pages.
Huang et al., "Performance comparison between polyvinylidene fluoride and polytetrafluoroethylene hollow fiber membranes for direct contact membrane distillation." Membranes 9.4, 52: 2019, 16 pages.
Hubadillah et al., "Green silica-based ceramic hollow fiber membrane for seawater desalination via direct contact membrane distillation," Separation and Purification Technology, 2018, 205:22-31, 10 pages.
Ingole et al., "Synthesis, characterization and surface modification of PES hollow fiber membrane support with polydopamine and thin film composite for energy generation," Chemical Engineering Journal, 2014, 243:137-146, 10 pages.
International Standard, "ISO 5667-3: Water quality—sampling—part 3: guidance on the preservation and handling of water samples," 3rd edn, Dec. 15, 2003, 38 pages.
International Standard, "ISO 9377-2: Water quality—determination of hydrocarbon oil index—Part 2: Method using solvent extraction and gas chromatography," First edition, Oct. 15, 2000, 24 pages.
IP 426/98, "Determination of the oil content of effluent water—extraction and infra-red spectrometric method," Oil in Water, IP 426, 2012, 5 pages.
Jansen et al., "On the unusual solvent and the effect on the gas transport in perfluorinated Hyflon AD Membranes," Journal of Membrane Science, Jan. 2007, 287(1):132-137, 6 pages.
Johnson et al., "The Molecular Complexity of Water in Organic Solvents Part II," J. Chem. Soc. A, Inorganic Phys. Theoretical, 1966, pp. 77-78, 2 pages.
Joseph et al., "Layer-by-Layer preparation of polyelectrolyte multilayer membranes for separation," Polymer Chemistry, 2014, 5:1817-1831, 19 pages.
Kado et al., "Diagnosis of atmospheric pressure low temperature plasma and application to high efficient methane conversion," Catal. Today, Feb. 2004, 89:47-55, 9 pages.
Kanna et al., "Estimating the Amount of Moisture Content in Crude Oil Samples," International Refereed Journal of Engineering and Science (IRJES), Feb. 2017, 6(2): 59-62, 4 pages.
Kaushik et al., "Microbubble technology: emerging field for water treatment," Bubble Science, Engineering and Technology, 2014, 6 pages.
Kazama et al., "Carbon dioxide and nitrogen transport properties of bis(phenyl)fluorene-based cardo polymer membranes," Journal of Membrane Science, 2002, 20:91-104, 14 pages.
Khalifeh et al., "Decomposition of methane to hydrogen using nanosecond pulsed plasma reactor with different active volumes, voltages and frequencies," Appl. Energy, May 2016, 169:585-596, 12 pages.
Khayet et al., "Robust surface modified polyetherimide hollow fiber membrane for long-term desalination by membrane distillation," Desalination, 2019, 466:107-117, 11 pages.
Khulbe et al., "Thin-film composite and/or thin film nanocomposite hollow fiber membrane for water treatment, pervaporation, and gas/vapor separation," Polymers 10 (2018) 1051, 22 pages.
Khuntia et al., "Microbubble-aided water and wastewater purification: A review," Reviews in Chemical Engineering, 2012, 28(4-6):191-221, 31 pages.
Kikkinides et al., "Gas Separation and Purification by Polymeric Adsorbents: Flue Gas Desulfurization and S02 Recovery with Styrenic Polymer," Ind. Eng. Chem. Res., Oct. 1993, 32(10):2365-2372, 8 pages.
Kim et al., "Effect of Demulsifier Partitioning on the Destabilization of Water-in-Oil Emulsions," Ind. Eng. Chem. Res., 1996, 35:1141-1149, 9 pages.
Kim et al., "Innovative swirling flow-type microbble generator for multi-stage DCMD desalination system: Focus on the two-phase flow pattern, bubble size distribution, and its effect on MD performance," Journal of Membrane Science, 2019, 588:117-197, 15 pages.
Kim et al., "Separation performance of PEBAX/PEI hollow fiber composite membrane for SO2/CO2/N2 mixed gas," Chemical Engineering Journal, Nov. 2013, 233:242-250.
Kirchnerová et al., "The Solubility of Water in Low-Dielectric Solvents," Can. J. Chem, Aug. 1976, 54(24):3909-3916, 8 pages.
Klaehn et al., "Humidified Gas stream Separation at High Temperatures Using Matrimid 5218," Separation Science and Technology, Nov. 2012, 47(14-15):2186-2191.
Knauss et al., "The solubility of p-xylene in water as a function of temperature and pressure and calculated thermodynamic quantities," Geochimica et Cosmochimica Acta, 1995, 59(12):2443-2448, 6 pages.
Ko et al., "Analysis of purge gas temperature in cyclic TSA process," Pergamon, Chemical Engineering Science, Jan. 2002, 57(1):179-195, 17 pages.
Kraftschik et al., "Dense film polyimide membranes for aggressive sour gas feed separations," Journal of Membrane Science, Feb. 2013, 428:608-619, 12 pages.
Kriebel, "Absorption, 2. Design of Systems and Equipment," Ullmann's Encyclopedia of Industrial Chemistry, 2012, 18 pages.
Lallemand et al., "Extending the treatment of highly sour gases: cryogenic distillation," Digital Refining: Processing, Operations & Maintenance, Jan. 2014, 8 pages.
Lallemand et al., "Highly sour gas processing: Bulk removal with SPREX Process," IPTC-10581-MS, International Petroleum Technology Conference, Nov. 2005, 18 pages.
Lallemand et al., "Solutions for the treatment of highly sour gases," Digital Refinding: Processing, Operations & Maintenance, Apr. 2012, 14 pages.
Lancia, et al., "Uncatalyzed heterogeneous oxidation of calcium bisulfite," Chemical Engineering Science, Aug. 1996, 51(16), 3889-3896.
Larbot et al., "Water desalination using ceramic membrane distillation," Desalination, 2004, 168:367-372, 6 pages.
Lau et al., "A recent progress in thin film composite membrane: A review," Desalination, 2012, 287, 11 pages.
Lau et al., "Progress in interfacial polymerization technique on composite membrane preparation," 2nd International Conference on Environmental Engineering and Applications, 2011, 5 pages.
Le-Clech et al., "Fouling in Membrane Bioreactors used in Wastewater Treatment," Journal of Membrane Science, 2006, 284:17-53, 37 pages.
Lee et al., "Diamine-Anchored Polystyrene Resins for Reversible SO2 Adsorption," ACS Sustainable Chem. Eng., Feb. 2016, 4(4), 8 pages.
Lee et al., "Influence of Microbubble in Physical Cleaning of MF Membrane Process for Wastewater Reuse," Environ Sci. Pollut. Res., Dec. 2014, 9 pages.
Lee et al., "The effect of aeration types on foulant removal in ex-situ chemical cleaning in place (CIP) with membranes fouled by secondary effluents," Chemical Engineering Journal, 2017, 333:730-738, 30 pages.
Li et al., "Fabrication of lab-scale hollow fiber membrane modules with high packing density," Separation and Purification Technology, 2004, 40:15-30, 16 pages.
Li et al., "Internally staged permeator prepared from annular hollow fibers for gas separation," AIChE Journal, 1998, 44:849-858, 10 pages.

(56) References Cited

OTHER PUBLICATIONS

Lin, "Energy Efficiency of Desalination: Fundamental Insights from Intuitive Interpretation," Environmental Science & Technology, 54: 2020, 76-84, 9 pages.

Liu et al., "Fabrication of a high-flux thin film composite hollow fiber nanofiltration membrane for wastewater treatment," Journal of Membrane Science, 2015, 478:25-36, 12 pages.

Liu et al., "A comparison of optimal internally staged permeator and external two-stage module design for O2 enrichment from air," Separation Science and Technology, 2001, 36(11):2385-2409, 27 pages.

Liu et al., "Effect of fiber variation on staged membrane gas separation module performance," AIChE Journal, 2001, 47(10):2206-2219, 14 pages.

Liu et al., "Non-thermal plasma approaches in CO2 utilization," Fuel Processing Technology, 1999, 58:119-134, 28 pages.

Lockhart, "Sour oil and gas management: 3.3," vol. III/New Developments: Energy, Transport, Sustainability Encyclopedia of Hydrocarbons, 2007, 34 pages.

Lokhandwala et al., "Membrane separation of nitrogen from natural gas: A case study from membrane synthesis to commercial deployment," Journal of Membrane Science, Jan. 2010, 346, 10 pages.

Louie et al., "Gas and liquid permeation properties of modified interfacial composite reverse osmosis membranes," Journal of Membrane Science, Dec. 2008, 325:793-800, 8 pages.

Lu et al., "Conversion of natural gas to C2 hydrocarbons via cold plasma technology," Journal of Natural Gas Chemistry, Jul. 2010, 19(4):375-379, 5 pages.

Luis et al., "Fundamental Modeling of Membrane Systems: Membrane and Process Performance," Elsevier Inc., 2018, 2 pages.

Luo et al., "Directional solvent for membrane-free water desalination—A molecular level study," Journal of Applied Physics, 110, 2011, 8 pages.

Maitre et al., "Plasma-enhanced catalysis for the upgrading of methane: A review of modelling and simulation methods," Reaction Chemistry & Engineering, Mar. 2020, 5:814-837, 23 pages.

Mandal et al., "M.A.L.D.I.-T.O.F. mass spectrometry characterization of 4-alkyl substituted phenol-formaldehyde novalac type resins," Polymer, 1997, 38(26):6267-6271, 5 pages.

Martínez-Salazar et al., "Hydrogen production by methane reforming with H2S using Mo. Cr/ZrO2—SBA15 and Mo, Cr/ZrO2—La2O3 catalyst," Int. J. Hydrogen Energy, Dec. 2015, 48:17272-17283, 12 pages.

Maruf, et al., "Influence of substrate processing and interfacial polymerization conditions on the surface topography and permselective properties of surface-patterned thin-film composite membranes," Journal of Membrane Science, 2016, 512:50-60, 11 pages.

Masi et al., "A neural network predictive model of pipeline internal corrosion profile," Proceedings of the 2014 First International Conference on Systems Informatics, Modeling and Simulation, Apr. 2014, 6 pages.

masterbond.com [online], "Epoxies with Low Coefficient of Thermal Expansion," available on or before May 12, 2015, via Internet Archive: Wayback Machine URL: <https://web.archive.org/web/20150512012852/https://www.masterbond.com/properties/epoxies-low-coefficient-thermal-expansion>, retrieved on Sep. 15, 2020, URL: <https://www.masterbond.com/properties/epoxies-low-coefficient-thermal-expansion>, 2 pages.

Mat et al., "Hollow fiber membrane modules," Current Opinion in Chemical Engineering, May 2014, 4, 7 pages.

Merkel et al., "Comparison of Hydrogen Sulfide Transport Properties in Fluorinated and Nonfluorinated Polymers," Macromolecules, Sep. 2006, 39(22):7591-7600.

Michell Instruments, "Impedance," Impedance Products, URL: <http://www.michell.com/uk/technology/impedence.htm> retrieved Sep. 9, 2019, 2 pages.

Mogildeea et al., "The assessment of carbon dioxide dissociation using a single-mode microwave plasma generator," Molecules, Mar. 2020, 25:1558, 10 pages.

Mohammadi et al., "Gas separation by silicone-coated dry asymmetric aromatic polyamide membranes," Gas Separation and Purification, 1995, 9(3), 7 pages.

Moradi et al., "Using PDMS coated TFC-RO membranes for CO2/N2 gas separation: Experimental study, modeling and optimization," Polymer Testing, Dec. 2016, 56, 12 pages.

Mosadegh-Sedghi et al., "Wetting phenomenon in membrane contactors—Causes and prevention," Journal of Membrane Science, 452: 2014, 332-353, 22 pages.

Naim et al., "Hydrophobic and hydrophillic hollow fiber membranes for CO2 stripping via gas-liquid membrane contractor," SciVerse Science Direct, Procedia Engineering, 2012, 44:328-331, 4 pages.

Neisi et al., "Effect of Mixing Efficiency in Dilution Water Consumption in a Crude Oil Desalting Plant," 2011, 3rd International Conference on Chemical, Biological and Environmental Engineering, 2011, 20:109-113, 5 pages.

Nijdam et al., "High performance micro-engineered hollow fiber membranes by smart sinneret design," Journal of Membrane Science, Jul. 2005, 256(1-2):209-215, 7 pages.

Ochered'ko et al., "Plasma-Chemical Conversion of Hydrogen Sulfide in the Atmosphere of Methane with Addition of CO2 and O2," Plasma Chem Plasma Process, Sep. 2017, 12 pages.

Odberg et al, "Studies of water in organic solvents using NMR and partition techniques-II Di-isopropyl ether, dibutyl phthalate and chloroform," Journal of Inorganic and Nuclear Chemistry, Aug. 1972, 34(8):2605-2616, 12 pages.

Oikawa et al., "Seawater Flue Gas Deslfurization: Its Technical Implications and Performance Results," Environmental Progress, Apr. 2003, 22(1):67-73, 7 pages.

Paidar et al., "Membrane electrolysis—History, current status and perspective," Electrochimica Acta., 2016, 209:737-756, 69 pages.

Palma et al., "A review about the recent advances in selected nonthermal plasma assisted solid-gas phase chemical processes," Nanomaterials, 2020, 10:1596, 56 pages.

PCT Application No. PCT/IB2019/061417, Lithoxoos et al., Regeneration Schemes for a Two Stage Adsorption Process for Claus Tail Gas Treatment, filed Dec. 28, 2019, 75 pages.

Peng et al. "Evolution of ultra-thin dense-selective layer from single-layer to dual-layer hollow fibers using novel Extem® polyetherimide for gas separation," Journal of Membrane Science, 2010, 360:48-57, 10 pages.

Peterson et al., "Novel polyamide composite membranes for gas separation prepared by interfacial polycondensation," Journal of Applied Polymer Science, 1996, 63(12):1557-1563, 7 pages.

Prince et al., "Nanofiber based triple layer hydro-philic/-phobic membrane—a solution for pore wetting in membrane distillation," Scientific Reports, 2014, 4, 6 pages.

Puliyalil et al., "A review of plasma-assisted catalytic conversion of gaseous dioxide and methane into value-added platform chemicals and fuels," The Royal Society of Chemistry, 2018, 8:27481-27508, 28 pages.

Ramakers et al., "Gliding arc plasmatron: Providing an alternative method for carbon dioxide conversion," ChemSusCHem, 2017, 10(12):2642-2652, 11 pages.

Ramasubramanian, "CO2 (H2S)-selective membranes for fuel cell hydrogen purification and flue gas carbon capture: an experimental and process modeling study", Dissertation for the degree of Doctor of Philosophy, Ohio state University, 2013, 270 pages.

Raynel et al., "A new method to select demulsifiers and optimize dosage at wet crude oil separation facilities," Oil & Gas Science and Technology—Rev. IFP Energies Nouvelles, 2021, 76(19), 11 pages.

Reddy et al., "Kinetics of hydrogen sulfide decomposition in a DBD plasma reactor operated at high temperature," Journal of Energy Chemistry, 2013, 22:382-386, 5 pages.

Ren et al., "Ionic liquids: Functionalization and absorption of SO2," Green Energy & Environment, Jul. 2018, 3(3):179-190, 12 pages.

Robeson, "The upper bound revisited," Journal of Membrane Science 320 (390-400), Jul. 15, 2008, 11 pages.

Roy et al., "Aspen-HYSYS Simulation of Natural Gas Processing Plant," Journal of Chemical Engineering, IEB, Dec. 2011, 26(1), 4 pages.

(56) References Cited

OTHER PUBLICATIONS

Rufford et al., "The removal of CO2 and N2 from natural gas: A review of conventional and emerging process technologies," Journal of Petroleum Science and Engineering 94-95: 123-154, Sep. 2012, 32 pages.
Sanap et al., "Analysis of saline water desalination by directed solvent extraction using octanoic acid, Desalination," 357: 2015, 150-162, 13 pages.
Schei et al., "Transient simulations of gas-oil-water separation plants," Modeling, Identification and Control, 1991, 12: 1 (27-46), 20 pages.
Schofield et al., "Factors affecting flux in membrane distillation," Desalination, 1990, 77:279-294, 16 pages.
Scribd [online], "Milling Practices and Procedures," available on or before Sep. 2017, retrieved from URL <https://www.scribd.com/document/358420338/Milling-Rev-2-Secured>, 80 pages.
Sensorland.com [online], "Impedance Moisture Sensor Technology, How Sensors work—Moisture Sensors," retrieved from URL: <http://www.sensorland.com/HowPage029.html>, retrieved Sep. 9, 2019, 2 pages.
Shell Global Solutions International BV, "Cansolv Technologies Inc. SO2 Scrubbing System" 2010, 2 pages.
Shirazi et al., "Direct contact membrane distillation for seawater desalination," Desalination and Water Treatment, 2012, 49(1-3):368-375, 9 pages.
Sidhoum et al., "An internally staged hollow-fiber permeator for gas separation," AIChE Journal, 1989, 35(5):764-774, 11 pages.
Simo et al., "Adsorption/Desorption of Water and Ethanol on 3A Zeolite in Near-Adiabatic Fixed Bed," Ind. Eng. Chem. Res., 48(20):9247-9260, 14 pages.
Sivalls et al., "Oil and Gas Separation Design Manual," Section: 300, Technical Bulletin, Feb. 10, 2009, 142:7, 63 pages.
Snoeckx et al. "Plasma technology—a novel solution for CO2 conversion?" Chem. Soc. Rev., 2017, 46:5805-5863, 59 pages.
Sofia et al., "Engineering Design Approaches for Minimum Fouling in Submerged MBR," Desalination, 2004, 160:67-74, 8 pages.
Sridhar et al., "Gas permeation properties of polyamide membrane prepared by interfacial polymerization," Journal of Material Science, 2007, 42, 10 pages.
Srisurichan et al., "Humic acid fouling in the membrane distillation process," Desalination, 2005, 174(1):63-72, 10 pages.
Stephenson et al., "Mutual solubility of water and aliphatic amines," Journal of Chemical & Engineering Data, 38: 1993, 625-629, 5 pages.
Sulfur recovery, Emissions Factors & AP 42, Compilation of Air Pollutant Emission Factors, Chapter 8.13, U.S. Environmental Protection Agency, Apr. 2015, 9 pages.
Sun et al., "Application of seawater to enhance SO2 removal from simulated flue gas through hollow fiber membrane contactor," Journal of Membrane Science, 2008, 312:6-14, 9 pages.
Tailor et al., "Supported Polytertiary Amines: Highly Efficient and Selective SO2 Adsorbents," Environ. Sci. Technol., Jan. 2014, 48(3):2025-2034.
tamintl.com [online], "TAM Scab Liner Systems," Tam International, available on or before Nov. 15, 2016 via Internet Archive Wayback Machine URL <https://web.archive.org/web/20161115203103/https://www.tamintl.com/images/pdfs/brochures/Scab_Liner_Brochure.pdf>, retrieved 2018, retrieved from URL <https://www.tamintl.com/images/pdfs/brochures/Scab_Liner_Brochure.pdf>, 4 pages.
Tan et al., "Inorganbic fibre membranes in catalytic processing," Current Opinion in Chemical Engineering, 2011, 1:69-76, 8 pages.
Teoh et al., "Investigation of different hollow fiber module designs for flux enhancement in the membrane distillation process," Journal of Membrane Science, 2008, 311(1-2):371-379, 9 pages.
Termpiyakul, "Heat and mass transfer characteristics of a direct contact membrane distillation process for desalination," Desalination, 2005, 177(1-3):133-141, 9 pages.
Vaisala [online], "Vaisala HUMICAP Sensor for Measuring Moisture in Oil," Technology Description, 2012, retrieved from URL: <https://www.vaisala.com/sites/default/files/documents/HUMICAP-for-Moisture-in-oil-B211231EN-A.pdf>, 2 pages.
Vasudevan, "Membranes and Diaphragms for Electrochemical Processes (Part-I)," Res. J. Chem. Sci., Feb. 2013, 3(2):1-3, 3 pages.
Vogt et al., "Comparison of membrane contactor and structured packings for CO2 absorption," Energy Procedia, 4: 2011, 1471-1477, 7 pages.
Volkov et al., "Amine-based solvents regeneration in gas-liquid membrane contactor based on asymmetric PVTMS," Petroleum Chemistry, 5: 2015, 716-723, 8 pages.
Wahedi et al., "Economic assessment of Temperature Swing Adsorption systems as Claus Tail Gas Clean up Units," Chemical Engineering Science, 2015, 126:186-195, 10 pages.
Wan et al., "Thin-film composite hollow fiber membrane with inorganic salt additives for high mechanical strength and high power density for pressure-retarded osmosis," Journal of Membrane Science, 2018, 555:388-397, 34 pages.
Wan et al., "Design and fabrication of hollow fiber membrane modules," Journal of Membrane Science, 2017, 538:96-107, 71 pages.
Wang et al., "Characterization of novel forward osmosis hollow fiber membranes," Journal of Membrane Science, 2010, 355, 10 pages.
Wang et al., "One-Step plasma-enabled catalytic carbon dioxide hydrogenation to higher hydrocarbons: Significance of Catalyst-Bed Configuration," Green Chemistry, Royal Society of Chemistry, 2021, 23:1642-1647, 6 pages.
Waterston et al., "Electrochemical oxidation of sulfide ion ata boron-doped diamond anode," Journal of applied electrochemistry, 2007, 37(3):367-373, 7 pages.
Weiland et al., "Distribution of HCN in sour water systems," Digital Refining, Apr. 2014, 5 pages.
Whitehead, "Plasma-catalysis: The known knowns, the known unknowns and the unknown unknowns," Journal of Physics, May 2016, 49:243001, 60 pages.
Wikipedia.com [online] "Thermal Diode," last revised Feb. 2019, retrieved on Oct. 7, 2019, retrieved from URL <https://en.wikipedia.org/wiki/Thermal_diode>, 2 pages.
Wikipedia.com [online], "Dielectric barrier discharge," Retrieved Oct. 29, 2021 from URL <https://en.wikipedia.org/wiki/Dielectric_barrier_discharge>, 7 pages.
Wu et al., "Effect of Demulsifier Properties on Destabilization of Water-in-Oil Emulsion," May 2003, Energy & Fuels, 2003, 17:1554-1559, 6 pages.
Wu et al., "Preparation and SO2 Absorption /Desorption Properties of Crosslinked Poly(1,1,3,3-Tetramethylguanidine Acrylate) Porous Particles," Macromolecular Rapid Communications, Nov. 2006, 27(22):1949-1954.
www.digitalrefining.com [online], "Labsorb: A regenerable wet scrubbing process for controlling SO2 emissions," Jan. 2001, retrieved on Jan. 11, 2022, retrieved from URL<https://www.digitalrefining.com/article/1000818/labsorb-a-regenerable-wet-scrubbing-process-for-controlling-so2-emissions#.Yd3Ha9HMKUk>, 2 pages.
Xia et al., "Efficient, Selective, and Reversible SO2 Capture with Highly Crosslinked Ionic Microgels via a Selective Swelling Mechanism," Advanced Functional Materials, Jan. 2018, 28(13):1704292.
Xia et al., "Structure design and applications of dual-layer polymeric membranes," Journal of Membrane Science, 2018, 562:85-111, 106 pages.
Xu et al., "Non-thermal plasma catalysis for CO2 conversion and catalyst design for the process," J. Phys. D: Appl. Phys. Mar. 2021, 54:233001, 20 pages.
Xuan et al., "Plasma oxidation of H2S over non-stoichiometric LaxMnO3 perovskite catalysts in a dielectric barrier discharge reactor," Catalysts, Aug. 2018, 8:317, 14 pages.
Yang et al., "Optimization of microstructural hollow fiber design for membrane distillation applications using CFD modeling," Journal of Membrane Science, 2012, 54 pages.
Yang et al., "Novel designs for improving the performance of hollow fiber membrane distillation modules," Journal of Membrane Science, 2011, 384(1-2):52-62, 37 pages.

(56) References Cited

OTHER PUBLICATIONS

Yang, "Chapter 2: Measurement of Oil in Produced Water," in Produced water, ed. K. Lee and J. Neff, pp. 57-88, Springer 2011, ISBN 978-1-4614-0045-5, 32 pages.

Yasukawa et al., "Preparation of a forward osmosis membrane using a highly porous polyketone microfiltration membrane as a novel support," Journal of Membrane Science, 2015, 487:51-59, 9 pages.

Ye et al., "Microbubble aeration enhances performance of vacuum membrane distillation desalination by alleviating membrane scaling," Water Research, 2018, 149:588-595, 30 pages.

Yun et al., "Direct contact membrane distillation mechanism for high concentration NaCl solutions," Desalination, 2006, 188(1-3):251-262, 12 pages.

Zhao et al., "Decomposition of hydrogen sulfide in non-thermal plasma aided by supported CdS and ZnS semiconductors," Green Chemistry, Apr. 2013, 15:1509-1513, 5 pages.

Zhao et al., "SO2 Absorption by Carboxylate Anion-Based Task-Specific Ionic Liquids: Effect of Solvents and Mechanism," Ind. Eng. Chem. Res., Dec. 2016, 55(50):12919-12928.

Zhao et al., "Status and progress of membrane contactors in post-combustion carbon capture: A state-of-the-art review of new developments," Journal of Membrane Science, 511, 2016, 180-206, 28 pages.

Zhou et al., "Interfacial polymerization on PES hollow fiber membranes using mixed diamines for nanofiltration removal of salts containing oxyanions and ferric ions," Desalination, 2016, 394:176-184, 9 pages.

Zou et al., "CO2—Selective polymeric membranes containing amines in crosslinked poly (vinyl alcohol)," Journal of Membrane Science, Dec. 2006, 286:310-321.

PCT International Search Report and Written Opinion in International Appln. No. PCT/US2022/052562, dated Apr. 24, 2023, 14 pages.

George et al., "A Review of Non-Thermal Plasma Technology: A novel solution for CO2 conversion and utilization," Renewable and Sustainable Energy Reviews, Aug. 2020, 135, 22 pages.

Reddy et al., "Catalytic packed bed non-thermal plasma reactor for the extraction of hydrogen from hydrogen sulfide," International Journal of Energy Research, May 2012, 37(11):1280-1286, 7 pages.

\* cited by examiner

CONVERSION OF HYDROGEN SULFIDE AND CARBON DIOXIDE INTO HYDROCARBONS USING NON-THERMAL PLASMA AND A CATALYST

TECHNICAL FIELD

This disclosure relates to conversion of hydrogen sulfide ($H_2S$) and carbon dioxide ($CO_2$) into hydrocarbons.

BACKGROUND

Hydrogen sulfide and carbon dioxide exist in various gas streams, including natural gas. Oil or gas that contains significant amounts of sulfur compounds like hydrogen sulfide is considered "sour", and oil refineries and gas processing plants utilize "sweetening" processes to remove such sulfur compounds. A typical sulfur recovery process includes liquid amine absorption and the Claus process. In liquid amine absorption, hydrogen sulfide and carbon dioxide are selectively removed from gas mixtures, and the hydrogen sulfide and carbon dioxide are flowed to the Claus process, which can convert the hydrogen sulfide into elemental sulfur. The Claus process utilizes oxygen to oxidize hydrogen sulfide into sulfur dioxide and water, and the sulfur dioxide reacts with hydrogen sulfide to produce elemental sulfur and water. The carbon dioxide, on the other hand, is typically released into the atmosphere without further use.

SUMMARY

Certain aspects of the subject matter described can be implemented as a method. A feed stream is flowed to a catalytic reactor. The catalytic reactor includes a non-thermal plasma and a catalyst. The feed stream includes hydrogen sulfide and carbon dioxide. The feed stream is contacted with the catalyst in the presence of the non-thermal plasma at a reaction temperature, thereby converting the hydrogen sulfide and the carbon dioxide in the feed stream to produce a product. The product includes a hydrocarbon and sulfur. The reaction temperature is in a range of from about 20 degrees Celsius (° C.) to about 900° C. The product is separated into a product stream and a sulfur stream. The product stream includes the hydrocarbon from the product. The sulfur stream includes the sulfur from the product.

This, and other aspects, can include one or more of the following features. In some implementations, the reaction temperature is in a range of from about 150° C. to about 250° C. In some implementations, the feed stream is contacted with the catalyst in the presence of the non-thermal plasma at a reaction pressure that is in a range of from about 1 bar to about 10 bar. In some implementations, the reaction pressure is about 1 bar. In some implementations, separating the product into the product stream and the sulfur stream includes condensing the sulfur, such that the sulfur stream is liquid. In some implementations, the catalyst includes a metal that includes at least one of molybdenum, cadmium, iron, cobalt, nickel, copper, zinc, chromium, palladium, or ruthenium. In some implementations, the catalyst includes a metal oxide that includes at least one of molybdenum oxide, cadmium oxide, iron oxide, cobalt oxide, nickel oxide, copper oxide, zinc oxide, chromium oxide, aluminum oxide, titanium oxide, zirconium oxide, gallium oxide, or magnesium oxide. In some implementations, the catalyst includes a metal sulfide that includes at least one of molybdenum sulfide, cadmium sulfide, iron sulfide, cobalt sulfide, nickel sulfide, copper sulfide, zinc sulfide, or chromium sulfide. In some implementations, the catalyst includes a zeolite-based catalyst that includes at least one of Zeolite Socony Mobil-5 (ZSM-5), titanium silicalite (TS-1), silicoaluminophosphate zeolite (SAPO-34), UOP zeolite material (UZM), mordenite (MOR), beta zeolite (BEA), or faujasite (FAU). In some implementations, the product stream includes at least one of methane or ethane. In some implementations, the non-thermal plasma is generated by a corona discharge, a dielectric barrier discharge, or a gliding arc discharge. In some implementations, the catalytic reactor includes a high voltage electrode, a dielectric barrier surrounding the catalyst, and a grounding electrode surrounding the dielectric barrier. In some implementations, the catalyst surrounds the high voltage electrode. In some implementations, a volumetric ratio of the hydrogen sulfide to the carbon dioxide in the feed stream is about 1:1.

Certain aspects of the subject matter described can be implemented as a method. A first feed stream is flowed to a first catalytic reactor. The first catalytic reactor includes a first non-thermal plasma and a first catalyst. The first feed stream includes hydrogen sulfide and carbon dioxide. The first feed stream is contacted with the first catalyst in the presence of the first non-thermal plasma at a first reaction temperature, thereby converting the hydrogen sulfide and the carbon dioxide in the first feed stream to produce a first intermediate product. The first intermediate product includes hydrogen, carbon monoxide, water, and sulfur. The first reaction temperature is in a range of from about 20 degrees Celsius (° C.) to about 900° C. The first intermediate product is separated into a second intermediate product and a first sulfur stream. The second intermediate product includes the hydrogen, the carbon monoxide, and the water from the first intermediate product. The first sulfur stream includes at least a portion of the sulfur from the first intermediate product. The second intermediate product is separated into a second feed stream and a second sulfur stream. The second feed stream includes the hydrogen, the carbon monoxide, and the water from the second intermediate product. The second sulfur stream includes at least a portion of the sulfur from the second intermediate product. The second feed stream is flowed to a second catalytic reactor. The second catalytic reactor includes a second non-thermal plasma and a second catalyst. The second feed stream is contacted with the second catalyst in the presence of the second non-thermal plasma at a second reaction temperature, thereby converting the hydrogen and the carbon monoxide in the second feed stream to produce a product. The product includes a hydrocarbon. The second reaction temperature is in a range of from about 20° C. to about 900° C.

This, and other aspects, can include one or more of the following features. In some implementations, the first reaction temperature and the second reaction temperature are in a range of from about 150° C. to about 250° C. In some implementations, the first feed stream is contacted with the first catalyst in the presence of the first non-thermal plasma at a first reaction pressure that is in a range of from about 1 bar to about 10 bar. In some implementations, the second feed stream is contacted with the second catalyst in the presence of the second non-thermal plasma at a second reaction pressure that is in a range of from about 1 bar to about 10 bar. In some implementations, the first reaction pressure and the second reaction pressure are about 1 bar. In some implementations, separating the first intermediate product into the second intermediate product and the first sulfur stream includes condensing at least a portion of the sulfur from the first intermediate product, such that the first sulfur stream is liquid. In some implementations, separating the second intermediate product stream into the second feed stream and the second sulfur stream includes contacting the second intermediate product stream with a solvent or a sorbent. In some implementations, the product includes at least one of methane or ethane. In some implementations, the first non-thermal plasma is generated by a first corona discharge, a first dielectric barrier discharge, or a first gliding arc discharge. In some implementations, the second non-thermal plasma is generated by a second corona discharge, a second dielectric barrier discharge, or a second gliding arc discharge. In some implementations, the first catalytic reactor includes a first high voltage electrode, a first dielectric barrier surrounding the first catalyst, and a first grounding electrode surrounding the first dielectric barrier. In some implementations, the first catalyst surrounds the first high voltage electrode. In some implementations, the second catalytic reactor includes a second high voltage electrode, a second dielectric barrier surrounding the second catalyst, and a second grounding electrode surrounding the second dielectric barrier. In some implementations, the second catalyst surrounds the second high voltage electrode.

The details of one or more implementations of the subject matter of this disclosure are set forth in the accompanying drawings and the description. Other features, aspects, and advantages of the subject matter will become apparent from the description, the drawings, and the claims.

DETAILED DESCRIPTION

This disclosure describes conversion of hydrogen sulfide ($H_2S$) and carbon dioxide ($CO_2$) into hydrocarbons. A feed stream including hydrogen sulfide and carbon dioxide is flowed to a reactor that includes a catalyst and non-thermal plasma. The feed stream contacts the catalyst in the presence of the non-thermal plasma at reaction conditions, thereby converting the hydrogen sulfide and the carbon dioxide to produce a product that includes hydrocarbon(s). Sulfur originating from the hydrogen sulfide can be separated from the product. The process can be implemented by a single-stage system or a multi-stage system. The subject matter described in this disclosure can be implemented in particular implementations, so as to realize one or more of the following advantages. In comparison to the Claus process, the methods and systems described in this disclosure do not require the addition of oxygen. Further, the methods and systems described in this disclosure produce valuable products, such as hydrocarbons and hydrogen gas. Carbon monoxide and carbon dioxide (known greenhouse gases) are used as feedstock to produce the aforementioned valuable products (hydrocarbons and hydrogen gas). The hydrogen originating from the hydrogen sulfide is not simply oxidized to produce water (as it does in the Claus process). Instead, the hydrogen originating from the hydrogen sulfide is a source for producing the aforementioned valuable products (hydrocarbons and hydrogen gas).

Figure 1A:
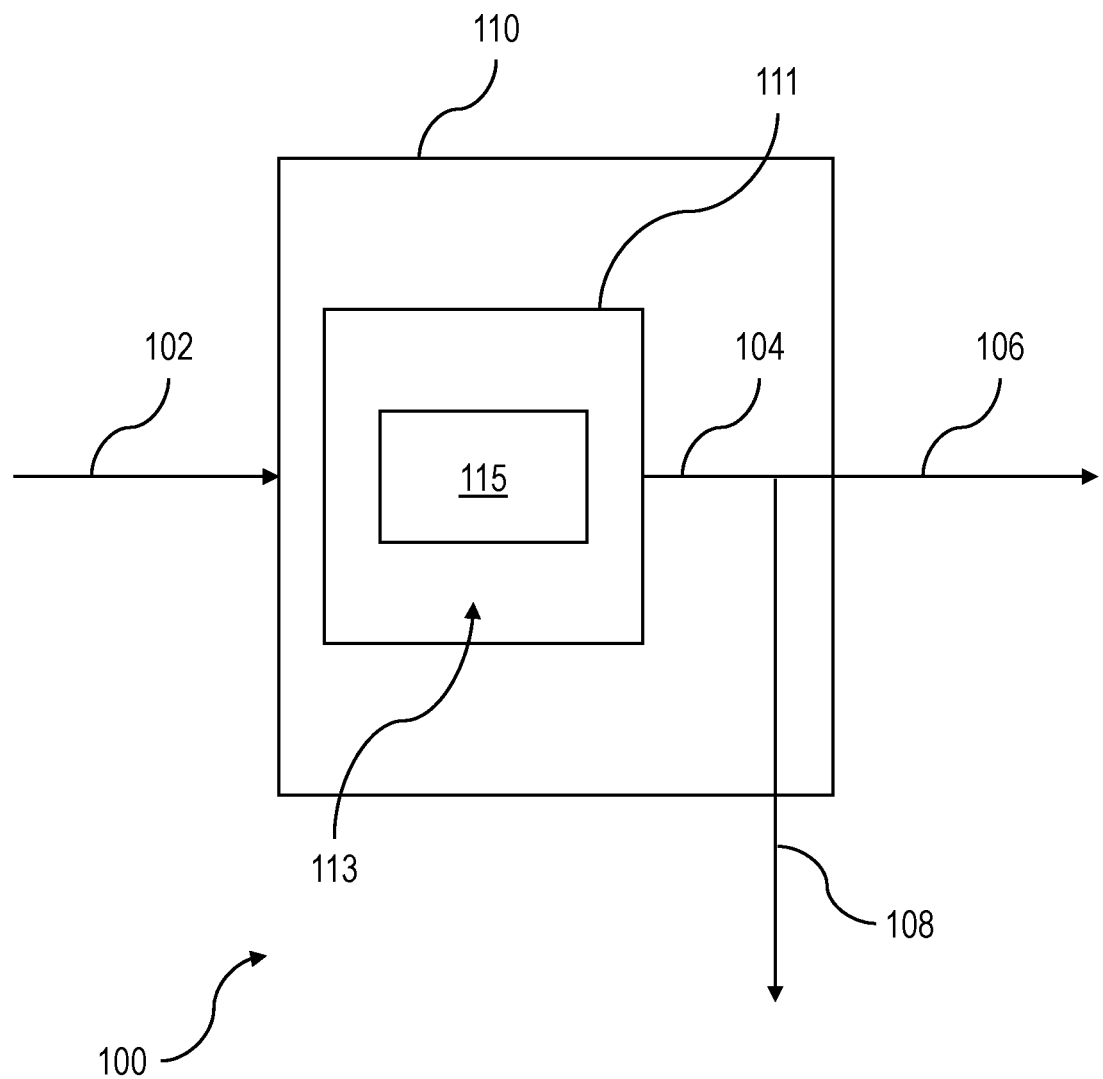
FIG. 1A is a schematic diagram of an example system for converting hydrogen sulfide and carbon dioxide into hydrocarbon(s).

FIG. 1A is a schematic diagram of an example system 100 for converting hydrogen sulfide and carbon dioxide into hydrocarbon(s). The system 100 includes a catalytic reaction unit 110. The catalytic reaction unit 110 includes a catalytic reactor 111. The catalytic reactor 111 includes a non-thermal plasma 113 and a catalyst 115. A feed stream 102 flows to the catalytic reactor 111. The feed stream 102 includes hydrogen sulfide and carbon dioxide. In some implementations, a volumetric ratio of the hydrogen sulfide to the carbon dioxide in the feed stream 102 is in a range of from about 9:1 to about 1:9. For example, the volumetric ratio of the hydrogen sulfide to the carbon dioxide in the feed stream 102 is about 1:1. The feed stream 102 can also include additional molecular compounds, such as water ($H_2O$, in the form of water vapor) and hydrocarbon(s). For example, the feed stream 102 can include molecular compounds typically present in a Claus feed (that is, a feed stream entering a Claus process reactor). In some implementations, the hydrogen sulfide and the carbon dioxide in the feed stream 102 is sufficient to generate the non-thermal plasma 113. In some implementations, the feed stream 102 also includes a gas that is used to facilitate generation of the non-thermal plasma 113. For example, the feed stream 102 can include an inert gas (such as nitrogen, helium, neon, and argon) or oxygen. Within the catalytic reactor 111, the feed stream 102 comes into contact with the catalyst 115 in the presence of the non-thermal plasma 113.

The catalyst 115 is configured to accelerate reaction(s) involving conversion of the hydrogen sulfide and the carbon dioxide in the feed stream 102. For example, the catalyst 115 can accelerate the conversion of hydrogen sulfide into hydrogen ($H_2$) and sulfur (S). For example, the catalyst 115 can accelerate the conversion of carbon dioxide into carbon monoxide (CO) and oxygen ($O_2$). In some implementations, the catalyst 115 is configured to shift the pathways of reaction(s) to selectively produce hydrocarbon(s) from carbon dioxide (from the feed stream 102), carbon monoxide (originating from the carbon dioxide from the feed stream 102), and hydrogen (originating from the hydrogen sulfide from the feed stream 102). For example, the catalyst 115 can accelerate reaction(s) between carbon dioxide and hydrogen to produce hydrocarbon(s) and water. For example, the catalyst 115 can accelerate reaction(s) between carbon monoxide and hydrogen to produce hydrocarbon(s) and water. In some implementations, the catalyst 115 is a supported metal-based catalyst. For example, the catalyst 115 can be a molybdenum-, cadmium-, iron-, cobalt-, nickel-, copper-, zinc-, chromium-, palladium-, or ruthenium-based catalyst supported on an aluminum oxide-, titanium oxide-, silicon oxide-, zirconium oxide-, lanthanum oxide-, cerium oxide-, magnesium oxide-, indium oxide-, or carbon-based support. In some implementations, the catalyst 115 is a metal oxide-based catalyst. For example, the catalyst 115 can be a molybdenum oxide-, cadmium oxide-, iron oxide-, cobalt oxide-, nickel oxide-, copper oxide-, zinc oxide-, chromium oxide-, aluminum oxide-, titanium oxide-, zirconium oxide-, gallium oxide-, or magnesium oxide-based catalyst. In some implementations, the catalyst 115 is a metal sulfide-based catalyst. For example, the catalyst 115 can be a molybdenum sulfide-, cadmium sulfide-, iron sulfide-, cobalt sulfide-, nickel sulfide-, copper sulfide-, zinc sulfide-, or chromium sulfide-based catalyst. In some implementations, the catalyst 115 is a zeolite-based catalyst. For example, the catalyst 115 can be a Zeolite Socony Mobil-5 (ZSM-5)-, titanium silicalite (TS-1)-, silicoaluminophosphate zeolite (SAPO-34)-, UOP zeolite material (UZM)-, mordenite (MOR)-, beta zeolite (BEA)-, or faujasite (FAU)-based catalyst.

The non-thermal plasma 113 is a plasma that is not in thermodynamic equilibrium. The non-thermal plasma 113 is not in thermodynamic equilibrium because the temperature of the electrons in the non-thermal plasma 113 is much greater than the temperature of the heavy species, such as the ions and the neutrals in the non-thermal plasma 113. The non-thermal plasma 113 is configured to promote dissociation of hydrogen sulfide and carbon dioxide. For example, the non-thermal plasma 113 can promote dissociation of hydrogen sulfide into hydrogen and sulfur. For example, the non-thermal plasma 113 can promote dissociation of carbon dioxide into carbon monoxide and oxygen. In some implementations, the non-thermal plasma 113 is generated by a corona discharge. In some implementations, the non-thermal plasma 113 is generated by a dielectric barrier discharge (DBD). In some implementations, the non-thermal plasma 113 is generated by a gliding arc discharge. A gliding arc discharge utilizes two diverging electrodes that are positioned such that their edges point toward each other to create a diverging discharge gap. In some implementations, the non-thermal plasma 113 is generated by an arc discharge. An arc discharge can generate the non-thermal plasma 113 between two electrodes with a similar or different geometry from the gliding arc discharge. An arc discharge is a low-current arc discharge, in contrast to a high-current thermal arc discharge.

The non-thermal plasma 113 and the catalyst 115 can operate synergistically within the catalytic reactor 111. For example, the non-thermal plasma 113 can activate and/or promote the catalyst 115. In some cases, the non-thermal plasma 113 can alter the adsorption/desorption equilibrium on a surface of the catalyst 115, which can lead to increased adsorption capabilities. In some cases, the non-thermal plasma 113 exposes the catalyst 115 to a discharge, which can lead to the formation of nanoparticles. The increased surface-to-volume ratio of nanoparticles can improve performance of the catalyst 115. In cases where the catalyst 115 is a metal oxide, the exposure of discharge from the non-thermal plasma 113 to the catalyst 115 can induce a reduction in the metal oxide of the catalyst 115, which can improve catalytic activity. In some cases, the non-thermal plasma 113 can reduce the probability and/or rate of coke formation. Coke formation can poison and/or deactivate the catalyst 115. Therefore, in such cases, the presence of the non-thermal plasma 113 can extend the operating life of the catalyst 115. As mentioned previously, the non-thermal plasma 113 can promote disassociation reactions, which can result in the production of radicals. In some cases, radicals can exhibit high sticking coefficients for transfer of electrons on the catalyst 115, thereby promoting catalytic activity. In some cases, the non-thermal plasma 113 contains photons which can potentially facilitate photocatalytic reactions in the presence of the catalyst 115, when a suitable catalyst is used. In some cases, the non-thermal plasma 113 vibrationally or electronically excite the hydrogen sulfide and/or carbon dioxide gas molecules, which can decrease an energy of dissociation when the gas molecules adsorb on a surface of the catalyst 115 in comparison to the gas molecules in their non-excited ground state. In the absence of the catalyst 115, the excited gas molecules may return to their ground state and emit the energy difference in the form of light. In some cases, the catalyst 115 can enhance the properties of the non-thermal plasma 113. For example, particles of the catalyst 115 with high electric constants can enhance the electric field strength for the non-thermal plasma 113. As another example, packing of the catalyst 115 can modify the nature of the discharge generating the non-thermal plasma 113 (such as changing the discharge from a microdischarge or streamer mode discharge to a more spatially confined, surface discharge). As another example, the chemical properties of the catalyst 115 can alter the non-thermal plasma 113 (such as, the catalyst 113 can have a high silicon to aluminum ratio, which can lead to a larger drop in electrical resistivity, thereby decreasing surface streamer propagation in the discharge generating the non-thermal plasma 113). As another example, in cases where the catalyst 115 is provided as a packed bed, the configuration of the packed bed within the electric field (which generates the non-thermal plasma 113) can generate local electric field enhancements due to inhomogeneity in the packed bed physical structure and/or surfaces of the catalyst 115. The surface charge accumulation in the packed bed can improve the properties of the non-thermal plasma 113. Similarly, the presence of random void spaces in the packed bed can also generate local electric field enhancements in the non-thermal plasma 113. The high intensity of the electric field in a locale can lead to the production of certain species (for example, desired hydrocarbons) that may not be observed in the bulk.

In some implementations, an operating temperature within the catalytic reactor 111 (also referred to as a reaction temperature) is in a range of from about 20 degrees Celsius (° C.) to about 900° C. In some implementations, the reaction temperature is in a range of from about 100° C. to about 300° C., in a range of from about 150° C. to about 250° C., or in a range of from about 150° C. to about 200° C. In some implementations, an operating pressure within the catalytic reactor 111 (also referred to as a reaction pressure) is in a range of from about 1 bar to about 10 bar. In some implementations, the reaction pressure is in a range of from about 1 bar to about 10 bar or in a range of from about 1 bar to about 5 bar. In some implementations, the reaction pressure is about 1 bar (atmospheric pressure).

Bringing the feed stream 102 into contact with the catalyst 115 in the presence of the non-thermal plasma 113 within the catalytic reactor 111 at the reaction temperature and the reaction pressure results in conversion of the hydrogen sulfide and the carbon dioxide in the feed stream 102 to produce a product 104. The product 104 includes a hydrocarbon and sulfur. In some implementations, the product 104 includes at least one of methane, ethane, or a hydrocarbon with more carbon atoms than ethane (such as propane and butane). The product 104 can also include additional molecular compounds, such as hydrogen, carbon monoxide, and water. In some cases, the product 104 also includes unreacted hydrogen sulfide and/or unreacted carbon dioxide from the feed stream 102.

The product 104 is separated into a product stream 106 and a sulfur stream 108. The product stream 106 includes the hydrocarbon from the product 104. In cases where the product 104 includes multiple hydrocarbons, the product stream 106 includes the hydrocarbons from the product 104. In cases where the product 104 includes unreacted hydrogen sulfide and/or unreacted carbon dioxide from the feed stream 102, the product stream 106 includes the unreacted hydrogen sulfide and/or unreacted carbon dioxide from the product 104. The sulfur stream 108 includes the sulfur from the product 104. In some implementations, separating the product 104 into the product stream 106 and the sulfur stream 108 includes cooling the product 104, such that a portion of the product 104 is condensed. For example, the catalytic reaction unit 110 can include a condenser (not shown), and the condenser can cool the product 104, such that a portion of the product 104 is condensed and separated from a remaining gaseous portion of the product 104. In such implementations, the condensed portion of the product 104 is the sulfur stream 108, and the remaining gaseous portion of the product 104 is the product stream 106. For example, the sulfur in the sulfur stream 108 can be liquid sulfur. In some implementations, the sulfur stream 108 includes additional condensable compounds in liquid form, such as water.

Figure 1B:
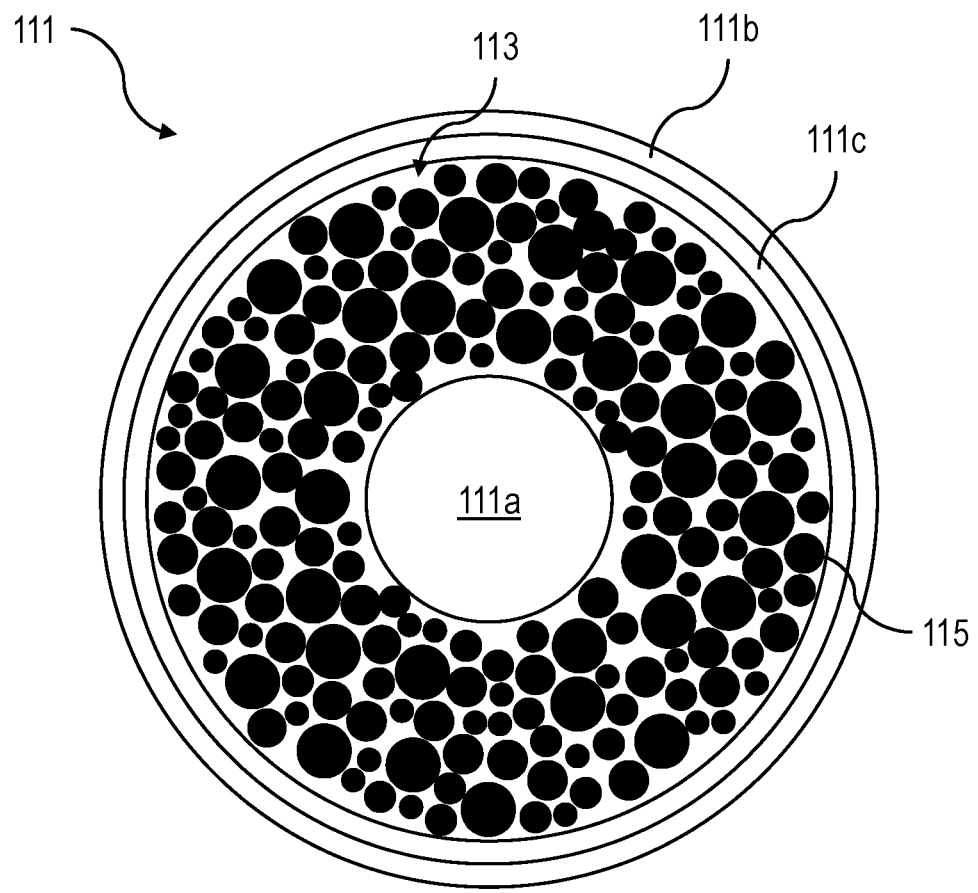
FIG. 1B is a cross-sectional view of an example catalytic reactor that can be implemented in the system of FIG. 1A.

FIG. 1B is a cross-sectional view of an example of the catalytic reactor 111. In some implementations, the catalytic reactor 111 includes a high voltage electrode 111a and a grounding electrode 111b. The high voltage electrode 111a uses a voltage in a range of from about 1 kilovolt (kV) to about 50 kV and works with the grounding electrode 111b to generate an electric field. In some implementations, the catalytic reactor 111 includes a dielectric barrier 111c. The dielectric barrier 111c can be included in between the electrodes 111a and 111b and serves as an electrically insulating material. The electrical discharge between the electrodes 111a and 111b separated by the dielectric barrier 111c (also referred to as a dielectric barrier discharge) interacts with the gas in the catalytic reactor 111 to generate the non-thermal plasma 113. The catalyst 115 can be disposed within the catalytic reactor 111 in a region of the catalytic reactor 111 where the dielectric barrier discharge generates the non-thermal plasma 113. For example (as shown in FIG. 1B), the high voltage electrode 111a can be centrally located within the catalytic reactor 111; the dielectric barrier 111c can circumferentially surround the high voltage electrode 111a; the grounding electrode 111b can circumferentially surround the dielectric barrier 111c; and the catalyst 115 can be disposed in the annular region between the high voltage electrode 111a and the dielectric barrier 111c. The annular region between the high voltage electrode 111a and the dielectric barrier 111c can also be the region in which the non-thermal plasma 113 is generated within the catalytic reactor 111. In some implementations (as shown in FIG. 1B), the catalyst 115 is provided within the catalytic reactor 111 in the form of a packed bed.

Figure 1C:
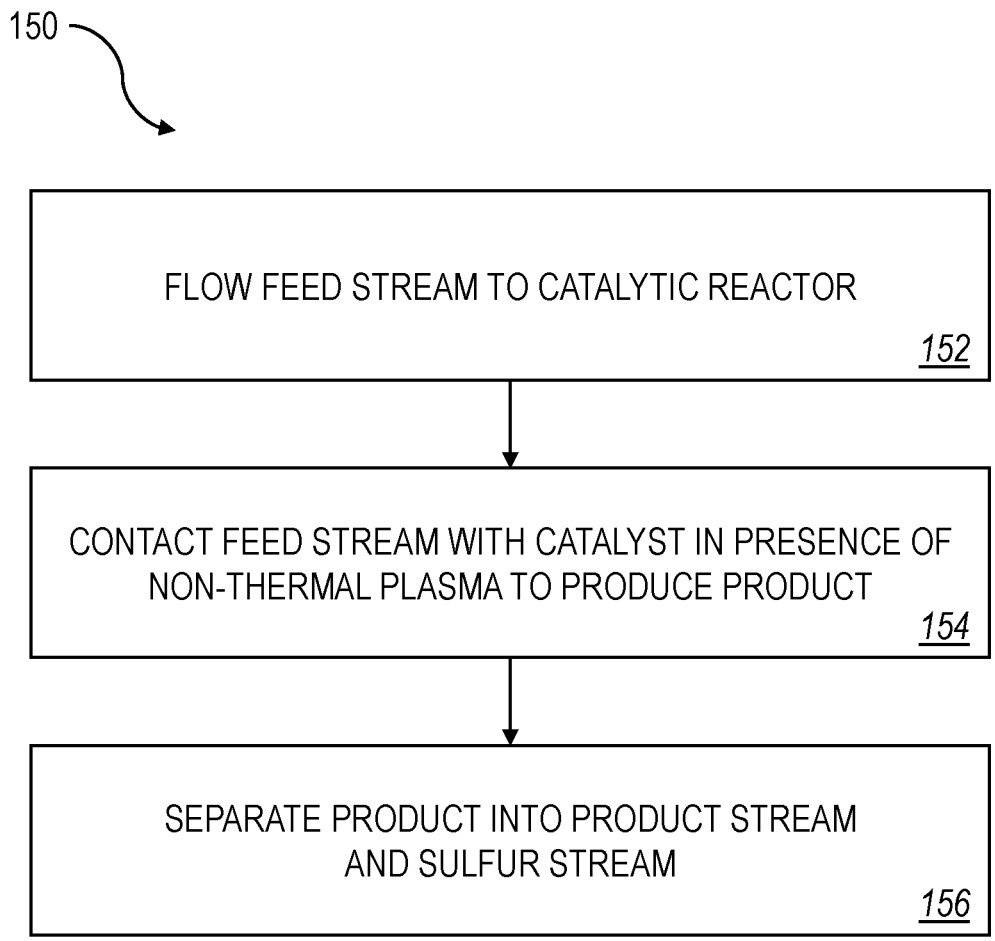
FIG. 1C is a flow chart of an example method for converting hydrogen sulfide and carbon dioxide into hydrocarbon(s).

FIG. 1C is a flow chart of an example method 150 for converting hydrogen sulfide and carbon dioxide into hydrocarbon(s). The system 100 can implement the method 150. At block 152 a feed stream (such as the feed stream 102) is flowed to a catalytic reactor (such as the catalytic reactor 111). As mentioned previously, the feed stream 102 includes hydrogen sulfide and carbon dioxide, and the catalytic reactor 111 includes the non-thermal plasma 113 and the catalyst 115. In some implementations, a volumetric ratio of the hydrogen sulfide to the carbon dioxide in the feed stream 102 at block 152 is about 1:1.

At block 154, the feed stream 102 is contacted with the catalyst 115 in the presence of the non-thermal plasma 113 within the catalytic reactor 111. The feed stream 102 is contacted with the catalyst 115 in the presence of the non-thermal plasma 113 at block 154 at a reaction temperature that is in a range of from about 20° C. to about 900° C. Contacting the feed stream 102 with the catalyst 115 in the presence of the non-thermal plasma 113 at block 154 results in converting the hydrogen sulfide and the carbon dioxide in the feed stream 102 to produce a product (such as the product 104). As mentioned previously, the product 104 includes a hydrocarbon and sulfur. In some implementations, the reaction temperature at block 154 is in a range of from about 100° C. to about 300° C., in a range of from about 150° C. to about 250° C., or in a range of from about 150° C. to about 200° C. In some implementations, an operating pressure within the catalytic reactor 111 (also referred to as a reaction pressure) at block 154 is in a range of from about 1 bar to about 10 bar. In some implementations, the reaction pressure at block 154 is in a range of from about 1 bar to about 10 bar or in a range of from about 1 bar to about 5 bar. In some implementations, the reaction pressure at block 154 is about 1 bar (atmospheric pressure).

At block 156, the product 104 is separated into a product stream (such as the product stream 106) and a sulfur stream (such as the sulfur stream 108). In some implementations, separating the product 104 into the product stream 106 and the sulfur stream 108 at block 156 includes cooling the product 104, such that a portion of the product 104 is condensed. In such implementations, the condensed portion of the product 104 is the sulfur stream 108, and the remaining gaseous portion of the product 104 is the product stream 106. As mentioned previously, the product stream 106 includes the hydrocarbon from the product 104. In cases where the product 104 includes multiple hydrocarbons, the product stream 106 includes the hydrocarbons from the product 104. For example, the product stream 106 includes methane, ethane, or both methane and ethane.

Figure 2A:
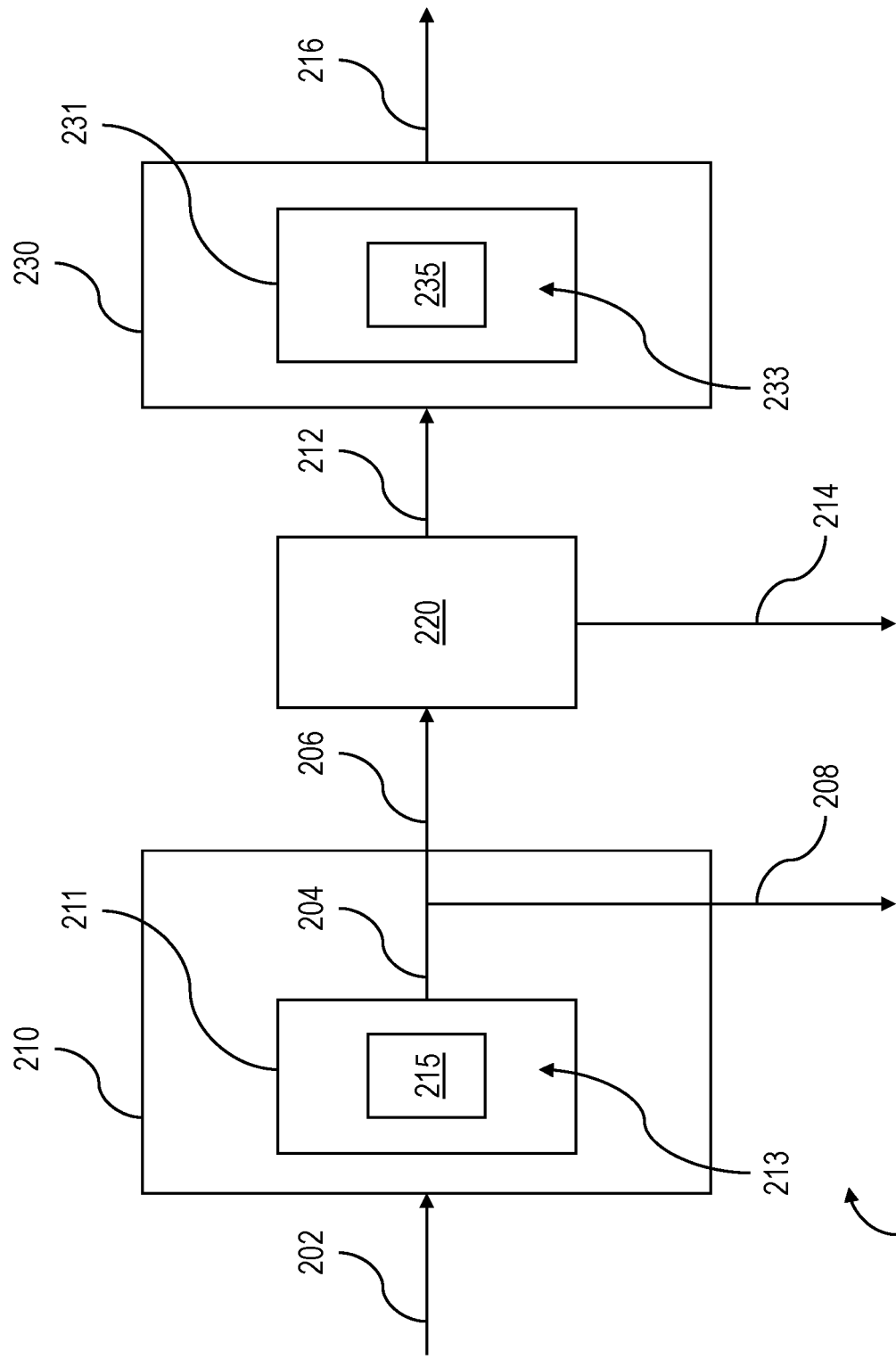
FIG. 2A is a schematic diagram of an example two-stage system for converting hydrogen sulfide and carbon dioxide into hydrocarbon(s).

FIG. 2A is a schematic diagram of an example two-stage system 200 for converting hydrogen sulfide and carbon dioxide into hydrocarbon(s). The two-stage system 200 shown in FIG. 2A can be substantially similar to the system 100 shown in FIG. 1A. The two-stage system 200 includes a first catalytic reaction unit 210. The first catalytic reaction unit 210 includes a first catalytic reactor 211. The first catalytic reactor 211 can be substantially similar or substantially the same to the catalytic reactor 111 shown in FIGS. 1A and 1B. The first catalytic reactor 211 includes a first non-thermal plasma 213 and a first catalyst 215. The first non-thermal plasma 213 can be substantially similar or substantially the same as the first non-thermal plasma 113 shown in FIGS. 1A and 1B. The first catalyst 215 can be substantially similar or substantially the same to the catalyst 115 shown in FIGS. 1A and 1B.

A first feed stream 202 flows to the first catalytic reactor 211. The first feed stream 202 can be substantially similar or substantially the same to the feed stream 102 shown in FIG. 1A. The feed stream 202 includes hydrogen sulfide ($H_2S$) and carbon dioxide ($CO_2$). In some implementations, a volumetric ratio of the hydrogen sulfide to the carbon dioxide in the feed stream 202 is in a range of from about 9:1 to about 1:9. For example, the volumetric ratio of the hydrogen sulfide to the carbon dioxide in the feed stream 202 is about 1:1. The first feed stream 202 can also include additional molecular compounds, such as water (for example, in the form of water vapor) and hydrocarbon(s). For example, the first feed stream 202 can include molecular compounds typically present in a Claus feed (that is, a feed stream entering a Claus process reactor). In some implementations, the hydrogen sulfide and the carbon dioxide in the feed stream 202 is sufficient to generate the non-thermal plasma 213. In some implementations, the first feed stream 202 also includes a gas that is used to facilitate generation of the first non-thermal plasma 213. For example, the first feed stream 202 can include an inert gas (such as nitrogen, helium, neon, and argon) or oxygen. Within the first catalytic reactor 211, the first feed stream 202 comes into contact with the first catalyst 215 in the presence of the first non-thermal plasma 213.

The first catalyst 215 is configured to accelerate reaction(s) involving conversion of the hydrogen sulfide and the carbon dioxide in the first feed stream 202. For example, the first catalyst 215 can accelerate the conversion of hydrogen sulfide into hydrogen ($H_2$) and sulfur (S). For example, the first catalyst 215 can accelerate the conversion of carbon dioxide into carbon monoxide (CO) and oxygen ($O_2$). In some implementations, the first catalyst 215 is configured to shift the pathways of reaction(s) to selectively produce hydrocarbon(s) from carbon dioxide (from the first feed stream 202), carbon monoxide (originating from the carbon dioxide from the first feed stream 202), and hydrogen (originating from the hydrogen sulfide from the first feed stream 202). For example, the first catalyst 215 can accelerate reaction(s) between carbon dioxide and hydrogen to produce hydrocarbon(s) and water. For example, the first catalyst 215 can accelerate reaction(s) between carbon monoxide and hydrogen to produce hydrocarbon(s) and water. In some implementations, the first catalyst 215 is a supported metal-based catalyst. For example, the first catalyst 215 can be a molybdenum-, cadmium-, iron-, cobalt-, nickel-, copper-, zinc-, chromium-, palladium-, or ruthenium-based catalyst supported on an aluminum oxide-, titanium oxide-, silicon oxide-, zirconium oxide-, lanthanum oxide-, cerium oxide-, magnesium oxide-, indium oxide-, or carbon-based support. In some implementations, the first catalyst 215 is a metal oxide-based catalyst. For example, the first catalyst 215 can be a molybdenum oxide-, cadmium oxide-, iron oxide-, cobalt oxide-, nickel oxide-, copper oxide-, zinc oxide-, chromium oxide-, aluminum oxide-, titanium oxide-, zirconium oxide-, gallium oxide-, or magnesium oxide-based catalyst. In some implementations, the first catalyst 215 is a metal sulfide-based catalyst. For example, the first catalyst 215 can be a molybdenum sulfide-, cadmium sulfide-, iron sulfide-, cobalt sulfide-, nickel sulfide-, copper sulfide-, zinc sulfide-, or chromium sulfide-based catalyst. In some implementations, the first catalyst 215 is a zeolite-based catalyst. For example, the first catalyst 215 can be a Zeolite Socony Mobil-5 (ZSM-5)-, titanium silicalite (TS-1)-, silicoaluminophosphate zeolite (SAPO-34)-, UOP zeolite material (UZM)-, mordenite (MOR)-, beta zeolite (BEA)-, or faujasite (FAU)-based catalyst.

The first non-thermal plasma 213 is a plasma that is not in thermodynamic equilibrium. The first non-thermal plasma 213 is not in thermodynamic equilibrium because the temperature of the electrons in the first non-thermal plasma 213 is much greater than the temperature of the heavy species, such as the ions and the neutrals in the first non-thermal plasma 213. The first non-thermal plasma 213 is configured to promote dissociation of hydrogen sulfide and carbon dioxide. For example, the first non-thermal plasma 213 can promote dissociation of hydrogen sulfide into hydrogen and sulfur. For example, the first non-thermal plasma 213 can promote dissociation of carbon dioxide into carbon monoxide and oxygen. In some implementations, the first non-thermal plasma 213 is generated by a corona discharge. In some implementations, the first non-thermal plasma 213 is generated by a dielectric barrier discharge. In some implementations, the first non-thermal plasma 213 is generated by a gliding arc discharge. In some implementations, the first non-thermal plasma 213 is generated by an arc discharge. Similar to the non-thermal plasma 113 and the catalyst 115 shown in FIGS. 1A and 1B, the first non-thermal plasma 213 and the first catalyst 215 can operate synergistically within the first catalytic reactor 211.

In some implementations, an operating temperature within the first catalytic reactor 211 (also referred to as a first reaction temperature) is in a range of from about 20° C. to about 900° C. In some implementations, the first reaction temperature is in a range of from about 100° C. to about 300° C., in a range of from about 150° C. to about 250° C., or in a range of from about 150° C. to about 200° C. In some implementations, an operating pressure within the first catalytic reactor 211 (also referred to as a first reaction pressure) is in a range of from about 1 bar to about 10 bar. In some implementations, the first reaction pressure is in a range of from about 1 bar to about 10 bar or in a range of from about 1 bar to about 5 bar. In some implementations, the first reaction pressure is about 1 bar (atmospheric pressure).

Bringing the first feed stream 202 into contact with the first catalyst 215 in the presence of the first non-thermal plasma 213 within the first catalytic reactor 211 at the first reaction temperature and the first reaction pressure results in conversion of the hydrogen sulfide and the carbon dioxide in the first feed stream 202 to produce a first intermediate product 204. The first intermediate product 204 includes hydrogen, carbon monoxide, water, and sulfur. In some implementations, the first intermediate product 204 includes a hydrocarbon. In some implementations, the first intermediate product 204 includes at least one of methane, ethane, or a hydrocarbon with more carbon atoms than ethane (such as propane and butane). The first intermediate product 204 can also include additional molecular compounds, such as unreacted hydrogen sulfide and unreacted carbon dioxide from the first feed stream 202.

The first intermediate product 204 is separated into a second intermediate product 206 and a first sulfur stream 208. The second intermediate product 206 includes the hydrogen, the carbon monoxide, and the water from the first intermediate product 204. In cases where the first intermediate product 204 includes hydrocarbon(s), the second intermediate product 206 includes the hydrocarbon(s) from the first intermediate product 204. In cases where the first intermediate product 204 includes unreacted hydrogen sulfide and/or unreacted carbon dioxide from the first feed stream 202, the second intermediate product 206 includes the unreacted hydrogen sulfide and/or unreacted carbon dioxide from the first intermediate product 204. The first sulfur stream 208 includes at least a portion of the sulfur from the first intermediate product 204. In some cases, the second intermediate product 206 includes a remaining portion of the sulfur from the first intermediate product 204 that is not separated into the first sulfur stream 208. For example, the second intermediate product 206 may include trace amounts of sulfur. In some implementations, separating the first intermediate product 204 into the second intermediate product 206 and the first sulfur stream 208 includes cooling the first intermediate product 204, such that a portion of the first intermediate product 204 is condensed. For example, the first catalytic reaction unit 210 can include a first condenser (not shown), and the first condenser can cool the first intermediate product 204, such that a portion of the first intermediate product 204 is condensed and separated from a remaining gaseous portion of the first intermediate product 204. In such implementations, the condensed portion of the first intermediate product 204 is the first sulfur stream 208, and the remaining gaseous portion of the first intermediate product 204 is the second intermediate product 206. For example, the sulfur in the first sulfur stream 208 can be liquid sulfur. In some implementations, the first sulfur stream 208 includes additional condensable compounds in liquid form, such as water.

The two-stage system 200 can include a sulfur removal unit 220. The second intermediate product 206 can flow to the sulfur removal unit 220. The second intermediate product 206 is separated into a second feed stream 212 and a second sulfur stream 214. The second feed stream 212 includes the hydrogen, the carbon monoxide, and the water from the second intermediate product 206. In cases where the second intermediate product 206 includes hydrocarbon(s), the second feed stream 212 includes the hydrocarbon(s) from the second intermediate product 206. In cases where the second intermediate product 206 includes unreacted hydrogen sulfide and/or unreacted carbon dioxide from the first intermediate product 204, the second feed stream 212 includes the unreacted hydrogen sulfide and/or unreacted carbon dioxide from the second intermediate product 206. The second sulfur stream 214 includes at least a portion of the sulfur from the second intermediate product 206. In some cases, the second sulfur stream 214 includes substantially all of the sulfur from the second intermediate product 206. For example, the second feed stream 212 includes zero sulfur/sulfur-containing compounds or a negligible amount of sulfur/sulfur-containing compounds. In some implementations, separating the second intermediate product 206 into the second feed stream 212 and the second sulfur stream 214 includes cooling the second intermediate product 206, such that a portion of the second intermediate product 206 is condensed. For example, the sulfur removal unit 220 can include a second condenser (not shown), and the second condenser can cool the second intermediate product 206, such that a portion of the second intermediate product 206 is condensed and separated from a remaining gaseous portion of the second intermediate product 206. In such implementations, the condensed portion of the second intermediate product 206 is the second sulfur stream 214, and the remaining gaseous portion of the second intermediate product 206 is the second intermediate product 212. For example, the sulfur in the second sulfur stream 214 can be liquid sulfur. In some implementations, the second sulfur stream 214 includes additional condensable compounds in liquid form, such as water. In some implementations, separating the second intermediate product 206 into the second feed stream 212 and the second sulfur stream 214 includes contacting the second intermediate product 206 with a solvent capable of dissolving sulfur compounds (extractive desulfurization). For example, the second intermediate product 206 can be contacted with polyethylene glycol (PEG) to preferentially solvate the sulfur from the second intermediate product 206. For example, the second intermediate product 206 can be contacted with an organic solvent through a low pressure drop packed column. Liquid sulfur can be extracted from the organic solvent by heating slightly hotter than the melting point of sulfur. In some implementations, separating the second intermediate product 206 into the second feed stream 212 and the second sulfur stream 214 includes contacting the second intermediate product 206 with a solid desulfurization sorbent (for example, a zinc oxide-based sorbent) to absorb, adsorb, or both absorb and adsorb sulfur from the second intermediate product 206.

The two-stage system 200 includes a second catalytic reaction unit 230. The second catalytic reaction unit 230 includes a second catalytic reactor 231. The second catalytic reactor 231 can be substantially similar or substantially the same to the catalytic reactor 111 shown in FIGS. 1A and 1B. In some implementations, the second catalytic reactor 231 is substantially similar or substantially the same as the first catalytic reactor 211. The second catalytic reactor 231 includes a second non-thermal plasma 233 and a second catalyst 235. The second non-thermal plasma 233 can be substantially similar or substantially the same as the first non-thermal plasma 113 shown in FIGS. 1A and 1B. In some implementations, the second non-thermal plasma 233 is substantially similar or substantially the same as the first non-thermal plasma 213. The second catalyst 235 can be substantially similar or substantially the same to the catalyst 115 shown in FIGS. 1A and 1B. In some implementations, the second catalyst 235 is substantially similar or substantially the same as the first catalyst 215.

The second feed stream 212 flows to the second catalytic reactor 231. Within the second catalytic reactor 231, the second feed stream 212 comes into contact with the second catalyst 235 in the presence of the second non-thermal plasma 233. The second catalyst 235 is configured to accelerate reaction(s) involving conversion of the hydrogen sulfide and the carbon dioxide in the second feed stream 212. For example, the second catalyst 235 can accelerate the conversion of hydrogen sulfide into hydrogen ($H_2$) and sulfur (S). For example, the second catalyst 235 can accelerate the conversion of carbon dioxide into carbon monoxide (CO) and oxygen ($O_2$). In some implementations, the second catalyst 235 is configured to shift the pathways of reaction(s) to selectively produce hydrocarbon(s) from carbon dioxide (for example, from the first feed stream 202), carbon monoxide (originating from the carbon dioxide from the first feed stream 202), and hydrogen (originating from the hydrogen sulfide from the first feed stream 202). For example, the second catalyst 235 can accelerate reaction(s) between carbon dioxide and hydrogen to produce hydrocarbon(s) and water. For example, the second catalyst 235 can accelerate reaction(s) between carbon monoxide and hydrogen to produce hydrocarbon(s) and water. In some implementations, the second catalyst 235 is a supported metal-based catalyst. For example, the second catalyst 235 can be a molybdenum-, cadmium-, iron-, cobalt-, nickel-, copper-, zinc-, chromium-, palladium-, or ruthenium-based catalyst supported on an aluminum oxide-, titanium oxide-, silicon oxide-, zirconium oxide-, lanthanum oxide-, cerium oxide-, magnesium oxide-, indium oxide-, or carbon-based support. In some implementations, the second catalyst 235 is a metal oxide-based catalyst. For example, the second catalyst 235 can be a molybdenum oxide-, cadmium oxide-, iron oxide-, cobalt oxide-, nickel oxide-, copper oxide-, zinc oxide-, chromium oxide-, aluminum oxide-, titanium oxide-, zirconium oxide-, gallium oxide-, or magnesium oxide-based catalyst. In some implementations, the second catalyst 235 is a metal sulfide-based catalyst. For example, the second catalyst 235 can be a molybdenum sulfide-, cadmium sulfide-, iron sulfide-, cobalt sulfide-, nickel sulfide-, copper sulfide-, zinc sulfide-, or chromium sulfide-based catalyst. In some implementations, the second catalyst 235 is a zeolite-based catalyst. For example, the second catalyst 235 can be a Zeolite Socony Mobil-5 (ZSM-5)-, titanium silicalite (TS-1)-, silicoaluminophosphate zeolite (SAPO-34)-, UOP zeolite material (UZM)-, mordenite (MOR)-, beta zeolite (BEA)-, or faujasite (FAU)-based catalyst. In some implementations, the second catalyst 235 is substantially similar or substantially the same as the first catalyst 215.

The second non-thermal plasma 233 is a plasma that is not in thermodynamic equilibrium. The second non-thermal plasma 233 is not in thermodynamic equilibrium because the temperature of the electrons in the second non-thermal plasma 233 is much greater than the temperature of the heavy species, such as the ions and the neutrals in the second non-thermal plasma 233. The second non-thermal plasma 233 is configured to promote dissociation of hydrogen sulfide and carbon dioxide. For example, the second non-thermal plasma 233 can promote dissociation of hydrogen sulfide into hydrogen and sulfur. For example, the second non-thermal plasma 233 can promote dissociation of carbon dioxide into carbon monoxide and oxygen. In some implementations, the second non-thermal plasma 233 is generated by a corona discharge. In some implementations, the second non-thermal plasma 233 is generated by a dielectric barrier discharge. In some implementations, the second non-thermal plasma 233 is generated by a gliding arc discharge. In some implementations, the second non-thermal plasma 233 is generated by an arc discharge. Similar to the non-thermal plasma 113 and the catalyst 115 shown in FIGS. 1A and 1B, the second non-thermal plasma 233 and the second catalyst 235 can operate synergistically within the second catalytic reactor 231. In some implementations, the second non-thermal plasma 233 is substantially similar or substantially the same as the first non-thermal plasma 213.

In some implementations, an operating temperature within the second catalytic reactor 231 (also referred to as a second reaction temperature) is in a range of from about 20° C. to about 900° C. In some implementations, the second reaction temperature is in a range of from about 100° C. to about 300° C., in a range of from about 150° C. to about 250° C., or in a range of from about 150° C. to about 200° C. In some implementations, the first reaction temperature within the first catalytic reactor 211 and the second reaction temperature within the second catalytic reactor 231 are substantially the same. In some implementations, an operating pressure within the second catalytic reactor 231 (also referred to as a first reaction pressure) is in a range of from about 1 bar to about 10 bar. In some implementations, the second reaction pressure is in a range of from about 1 bar to about 10 bar or in a range of from about 1 bar to about 5 bar. In some implementations, the second reaction pressure is about 1 bar (atmospheric pressure). In some implementations, the first reaction pressure within the first catalytic reactor 211 and the second reaction pressure within the second catalytic reactor 231 are substantially the same.

The selection of the first catalyst 215 and the second catalyst 235 can be decided based on various factors. For example, the first catalyst 215 may be selected to be a catalyst that resists sulfur poisoning (such as a supported or unsupported metal sulfide-based catalyst), and the second catalyst 235 may be selected to be a catalyst that better enhances hydrogenation reactions of carbon monoxide and carbon dioxide to produce hydrocarbons in comparison to the first catalyst 215 but may be sensitive to sulfur poisoning (such as a metal-based catalyst). The first reaction temperature and first reaction pressure can be selected to optimize the desired reactions in the first catalytic reactor 211 based on the selected first catalyst 215. Similarly, the second reaction temperature and second reaction pressure can be selected to optimize the desired reactions in the second catalytic reactor 231 based on the selected second catalyst 235.

Bringing the second feed stream 212 into contact with the second catalyst 235 in the presence of the second non-thermal plasma 233 within the second catalytic reactor 231 at the second reaction temperature and the second reaction pressure results in conversion of the hydrogen sulfide and the carbon dioxide in the second feed stream 212 to produce a product 216. The product 216 includes hydrocarbon(s). In some implementations, the product 216 includes at least one of methane, ethane, or a hydrocarbon with more carbon atoms than ethane (such as propane and butane). The product 216 can also include additional molecular compounds, such as unreacted carbon dioxide from the second feed stream 212, carbon monoxide, hydrogen, and water (for example, in the form of water vapor). In some implementations, the product 216 includes zero sulfur/sulfur-containing compounds or a negligible amount of sulfur/sulfur-containing compounds.

Figure 2B:
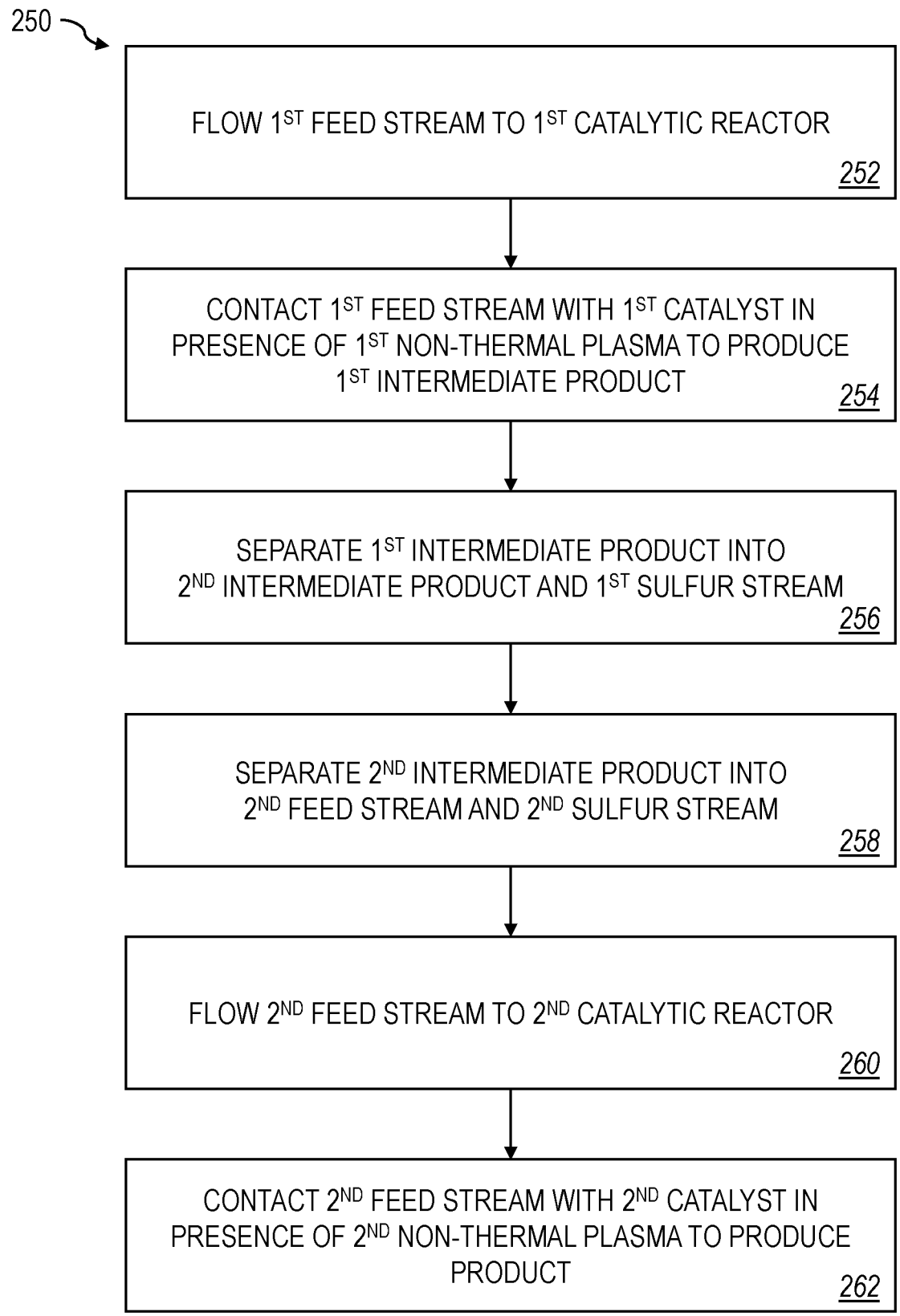
FIG. 2B is a flow chart of an example two-stage method for converting hydrogen sulfide and carbon dioxide into hydrocarbon(s).

FIG. 2B is a flow chart of an example two-stage method 250 for converting hydrogen sulfide and carbon dioxide into hydrocarbon(s). The two-stage system 200 can implement the method 250. At block 252 a first feed stream (such as the first feed stream 202) is flowed to a first catalytic reactor (such as the first catalytic reactor 211). As mentioned previously, the first feed stream 202 includes hydrogen sulfide and carbon dioxide, and the first catalytic reactor 211 includes the first non-thermal plasma 213 and the first catalyst 215. In some implementations, a volumetric ratio of the hydrogen sulfide to the carbon dioxide in the first feed stream 202 at block 252 is about 1:1.

At block 254, the first feed stream 202 is contacted with the first catalyst 215 in the presence of the first non-thermal plasma 213 within the first catalytic reactor 211. The first feed stream 202 is contacted with the first catalyst 215 in the presence of the first non-thermal plasma 213 at block 254 at a first reaction temperature that is in a range of from about 20° C. to about 900° C. Contacting the first feed stream 202 with the first catalyst 215 in the presence of the first non-thermal plasma 213 at block 254 results in converting the hydrogen sulfide and the carbon dioxide in the first feed stream 202 to produce a first intermediate product (such as the first intermediate product 204). As mentioned previously, the first intermediate product 204 includes a hydrogen, carbon monoxide, water, and sulfur. In some implementations, the first reaction temperature at block 254 is in a range of from about 100° C. to about 300° C., in a range of from about 150° C. to about 250° C., or in a range of from about 150° C. to about 200° C. In some implementations, an operating pressure within the first catalytic reactor 211 (also referred to as a first reaction pressure) at block 254 is in a range of from about 1 bar to about 10 bar. In some implementations, the first reaction pressure at block 254 is in a range of from about 1 bar to about 10 bar or in a range of from about 1 bar to about 5 bar. In some implementations, the first reaction pressure at block 254 is about 1 bar (atmospheric pressure).

At block 256, the first intermediate product 204 is separated into a second intermediate product (such as the second intermediate product 206) and a first sulfur stream (such as the first sulfur stream 208). As mentioned previously, the first sulfur stream 208 includes at least a portion of the sulfur from the first intermediate product 204. In some cases, the second intermediate product 206 includes a remaining portion of the sulfur from the first intermediate product 204 that is not separated into the first sulfur stream 208. For example, the second intermediate product 206 may include trace amounts of sulfur. In some implementations, separating the first intermediate product 204 into the second intermediate product 206 and the first sulfur stream 208 at block 256 includes cooling the first intermediate product 204, such that a portion of the first intermediate product 204 is condensed. In such implementations, the condensed portion of the first intermediate product 204 is the first sulfur stream 208, and the remaining gaseous portion of the first intermediate product 204 is the second intermediate product 206. As mentioned previously, the second intermediate product 206 includes the hydrogen, the carbon monoxide, and the water from the first intermediate product 204. In cases where the first intermediate product 204 includes hydrocarbon(s), the second intermediate product 206 includes the hydrocarbon(s) from the first intermediate product 204. For example, the second intermediate product 206 includes methane, ethane, or both methane and ethane.

At block 258, the second intermediate product 206 is separated into a second feed stream (such as the second feed stream 212) and a second sulfur stream (such as the second sulfur stream 214). As mentioned previously, the second feed stream 212 includes the hydrogen, the carbon monoxide, and the water from the second intermediate product 206. The second feed stream 212 can also include unreacted carbon dioxide from the first feed stream 202. As mentioned previously, the second sulfur stream 214 includes at least a portion of the sulfur from the second intermediate product 206.

At block 260, the second feed stream 212 is flowed to a second catalytic reactor (such as the second catalytic reactor 231). As mentioned previously, the second catalytic reactor 231 includes the second non-thermal plasma 233 and the second catalyst 235.

At block 262, the second feed stream 212 is contacted with the second catalyst 235 in the presence of the second non-thermal plasma 233. The second feed stream 212 is contacted with the second catalyst 235 in the presence of the second non-thermal plasma 233 within the second catalytic reactor 231 at block 262 at a second reaction temperature that is in a range of from about 20° C. to about 900° C. In some implementations, the second reaction temperature at block 262 is in a range of from about 100° C. to about 300° C., in a range of from about 150° C. to about 250° C., or in a range of from about 150° C. to about 200° C. In some implementations, an operating pressure within the second catalytic reactor 231 (also referred to as a second reaction pressure) at block 262 is in a range of from about 1 bar to about 10 bar. In some implementations, the second reaction pressure at block 262 is in a range of from about 1 bar to about 10 bar or in a range of from about 1 bar to about 5 bar. In some implementations, the second reaction pressure at block 262 is about 1 bar (atmospheric pressure).

Contacting the second feed stream 212 with the second catalyst 235 in the presence of the second non-thermal plasma 233 at block 262 results in converting the hydrogen and the carbon monoxide in the second feed stream 212 to produce a product (such as the product 216). As mentioned previously, the product 216 includes hydrocarbon(s). In some implementations, the product 216 includes at least one of methane, ethane, or a hydrocarbon with more carbon atoms than ethane (such as propane and butane). The product 216 can also include additional molecular compounds, such as unreacted carbon dioxide from the second feed stream 212, carbon monoxide, hydrogen, and water (for example, in the form of water vapor). In some implementations, the product 216 includes zero sulfur/sulfur-containing compounds or a negligible amount of sulfur/sulfur-containing compounds.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

As used in this disclosure, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

As used in this disclosure, the term "about" or "approximately" can allow for a degree of variability in a value or range, for example, within 10%, within 5%, or within 1% of a stated value or of a stated limit of a range.

As used in this disclosure, the term "substantially" refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "0.1% to about 5%" or "0.1% to 5%" should be interpreted to include about 0.1% to about 5%, as well as the individual values (for example, 1%, 2%, 3%, and 4%) and the sub-ranges (for example, 0.1% to 0.5%, 1.1% to 2.2%, 3.3% to 4.4%) within the indicated range. The statement "X to Y" has the same meaning as "about X to about Y," unless indicated otherwise. Likewise, the statement "X, Y, or Z" has the same meaning as "about X, about Y, or about Z," unless indicated otherwise.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described components and systems can generally be integrated together or packaged into multiple products.

Accordingly, the previously described example implementations do not define or constrain the present disclosure. Other changes, substitutions, and alterations are also possible without departing from the spirit and scope of the present disclosure.

What is claimed is:

1. A method comprising:
   flowing a feed stream to a catalytic reactor comprising a non-thermal plasma and a catalyst, the feed stream comprising hydrogen sulfide and carbon dioxide, the catalyst comprising a zeolite-based catalyst;
   contacting the feed stream with the catalyst in the presence of the non-thermal plasma at a reaction temperature that is in a range of from about 20 degrees Celsius (° C.) to about 900° C., thereby converting the hydrogen sulfide and the carbon dioxide in the feed stream to produce a product comprising a hydrocarbon and sulfur, the hydrocarbon having more carbon atoms than ethane; and
   separating the product into a product stream comprising the hydrocarbon and a sulfur stream comprising the sulfur.

2. The method of claim 1, wherein the reaction temperature is in a range of from about 150° C. to about 250° ° C.

3. The method of claim 2, wherein the feed stream is contacted with the catalyst in the presence of the non-thermal plasma at a reaction pressure that is in a range of from about 1 bar to about 10 bar.

4. The method of claim 3, wherein the reaction pressure is about 1 bar.

5. The method of claim 3, wherein separating the product into the product stream and the sulfur stream comprises condensing the sulfur, such that the sulfur stream is liquid.

6. The method of claim 5, wherein the zeolite-based catalyst is selected from the group consisting of a Zeolite Socony Mobil-5 (ZSM-5), titanium silicalite (TS 1), silicoaluminophosphate zeolite (SAPO-34), UOP zeolite material (UZM), mordenite (MOR), beta zeolite (BEA), or faujasite (FAU) based catalyst.

7. The method of claim 5, wherein the product stream comprises at least one of methane or ethane.

8. The method of claim 5, wherein the non-thermal plasma is generated by a corona discharge, a dielectric barrier discharge, or a gliding arc discharge.

9. The method of claim 8, wherein the catalytic reactor comprises:
   a high voltage electrode;
   the catalyst surrounding the high voltage electrode;
   a dielectric barrier surrounding the catalyst; and
   a grounding electrode surrounding the dielectric barrier.

10. The method of claim 9, wherein a volumetric ratio of the hydrogen sulfide to the carbon dioxide in the feed stream is about 1:1.

11. A method comprising:
    flowing a first feed stream to a first catalytic reactor comprising a first non-thermal plasma and a first catalyst, the first feed stream comprising hydrogen sulfide and carbon dioxide;
    contacting the first feed stream with the first catalyst in the presence of the first non-thermal plasma at a first reaction temperature that is in a range of from about 20 degrees Celsius (° C.) to about 900° ° C., thereby converting the hydrogen sulfide and the carbon dioxide in the first feed stream to produce a first intermediate product comprising hydrogen, carbon monoxide, water, and sulfur;
    separating the first intermediate product into a second intermediate product comprising the hydrogen, the carbon monoxide, and the water and a first sulfur stream comprising at least a portion of the sulfur from the first intermediate product;
    separating the second intermediate product into a second feed stream comprising the hydrogen, the carbon monoxide, and the water and a second sulfur stream comprising at least a portion of the sulfur from the second intermediate product;
    flowing the second feed stream to a second catalytic reactor comprising a second non-thermal plasma and a second catalyst, the second catalyst comprising a zeolite-based catalyst; and
    contacting the second feed stream with the second catalyst in the presence of the second non-thermal plasma at a second reaction temperature that is in a range of from about 20° C. to about 900° C., thereby converting the hydrogen and the carbon monoxide in the second feed stream to produce a product comprising a hydrocarbon having more carbon atoms than ethane.

12. The method of claim 11, wherein the first reaction temperature and the second reaction temperature are in a range of from about 150° C. to about 250° C.

13. The method of claim 12, wherein the first feed stream is contacted with the first catalyst in the presence of the first non-thermal plasma at a first reaction pressure that is in a range of from about 1 bar to about 10 bar, and the second feed stream is contacted with the second catalyst in the presence of the second non-thermal plasma at a second reaction pressure that is in a range of from about 1 bar to about 10 bar.

14. The method of claim 13, wherein the first reaction pressure and the second reaction pressure are about 1 bar.

15. The method of claim 13, wherein separating the first intermediate product into the second intermediate product stream and the first sulfur stream comprises condensing at least the portion of the sulfur from the first intermediate product, such that the first sulfur stream is liquid.

16. The method of claim 15, wherein separating the second intermediate product stream into the second feed stream and the second sulfur stream comprises contacting the second intermediate product stream with a solvent or a sorbent.

17. The method of claim 16, wherein the product comprises at least one of methane or ethane.

18. The method of claim 16, wherein the first non-thermal plasma is generated by a first corona discharge, a first dielectric barrier discharge, or a first gliding arc discharge, and the second non-thermal plasma is generated by a second corona discharge, a second dielectric barrier discharge, or a second gliding arc discharge.

19. The method of claim 18, wherein:
    the first catalytic reactor comprises:
      a first high voltage electrode;
      the first catalyst surrounding the first high voltage electrode;
      a first dielectric barrier surrounding the first catalyst; and
      a first grounding electrode surrounding the first dielectric barrier; and
    the second catalytic reactor comprises:
      a second high voltage electrode;
      the second catalyst surrounding the second high voltage electrode;
      a second dielectric barrier surrounding the second catalyst; and
      a second grounding electrode surrounding the second dielectric barrier.

* * * * *